US006936615B2

(12) United States Patent
Emig et al.

(10) Patent No.: US 6,936,615 B2
(45) Date of Patent: *Aug. 30, 2005

(54) HETEROARYL DERIVATIVES AND THEIR USE AS MEDICAMENTS

(75) Inventors: Peter Emig, Bruchköbel (DE); Eckhard Günther, Maintal (DE); Jürgen Schmidt, Uhldingen-Mühofen (DE); Bernd Nickel, Mühltal (DE); Bernhard Kutscher, Maintal (DE)

(73) Assignee: Zentaris GmbH, Frankfurt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/741,310

(22) Filed: Dec. 19, 2003

(65) Prior Publication Data

US 2004/0132747 A1 Jul. 8, 2004

Related U.S. Application Data

(63) Continuation of application No. 09/910,141, filed on Jul. 20, 2001.

(30) Foreign Application Priority Data

Jul. 21, 2000 (DE) .......................................... 100 35 928

(51) Int. Cl.[7] .................... C07D 403/12; C07D 403/14; A61K 31/496; A61K 31/506; A61P 35/02
(52) U.S. Cl. .................. 514/253.02; 544/333; 544/361; 514/256
(58) Field of Search ................................. 544/333, 361; 514/253.02, 256

(56) References Cited

U.S. PATENT DOCUMENTS

| | | | |
|---|---|---|---|
| 4,656,174 A | * | 4/1987 | Campbell et al. ...... 514/253.06 |
| 4,937,246 A | * | 6/1990 | Sugihara et al. ....... 514/254.11 |
| 5,432,175 A | | 7/1995 | Dyke et al. |
| 5,804,588 A | | 9/1998 | Dyke et al. |
| 5,861,395 A | | 1/1999 | Taveras et al. |
| 6,706,722 B2 | * | 3/2004 | Emig et al. ................. 514/269 |

FOREIGN PATENT DOCUMENTS

| | | |
|---|---|---|
| EP | 0112 776 A2 | 7/1984 |
| EP | 0 831 090 A1 | 3/1998 |
| WO | WO 95/00497 | 1/1995 |
| WO | WO 97/44329 | 11/1997 |
| WO | WO 98/00402 | 1/1998 |
| WO | WO 99/02520 * | 1/1999 |
| WO | WO 99/16751 | 4/1999 |
| WO | WO 00/12074 | 3/2000 |
| WO | WO 00/51614 | 9/2000 |

OTHER PUBLICATIONS

Chemical Abstract, abstract of WO 99/02520.*
Examination Report of the corresponding Chinese Patent Application.
Todd R. Elworthy, Anthony P.D.W. Ford, Gary W. Bantle, et al., N–Arylpiperazinyl–N'–propylamino Derivatives of Heteroaryl Amides as Functional Uroselective a1–Adrenoceptor Antagaonists, J. Med. Chem. 1997, 40, 2674–2687.
Arthur G. Taveras, Jeff Deskus, Jianping Chao, Cynthia J. Caccaro, et al., Identification of Pharmacokinetically Stable 3, 10–Dibromo–8–chlorobenzocycloheptapyridine Farnesyl Protein Transferase Inhibitors with Potent Enzyme and Cellular Activities, J. Med Chem. 1999, 42, 2651–2661.
El–Sebai A. Ibrahim, I. Chaaban and S. M. El–Khawass, Synthesis of Some Quinoline Derivatives of Potential Anti-amebic Activity, Pharmazie 32, H. 3 (1977), 155–156.

* cited by examiner

Primary Examiner—Mark L. Berch
Assistant Examiner—Kahsay Habte
(74) Attorney, Agent, or Firm—Goodwin Procter, LLP

(57) ABSTRACT

The invention relates to novel quinoline derivatives of the formula 1, to their preparation and to their use as medicaments, in particular for treating tumors.

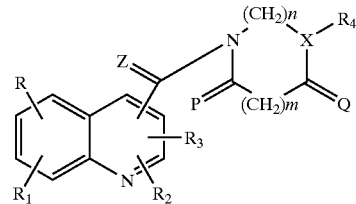

14 Claims, No Drawings

HETEROARYL DERIVATIVES AND THEIR USE AS MEDICAMENTS

RELATED APPLICATION

This application is a continuation of co-pending application Ser. No. 09/910,141 filed Jul. 20, 2001.

FIELD OF THE INVENTION

The invention relates to novel heteroaryl derivatives of the formula 1, to their preparation and to their use as medicaments, in particular for treating tumors.

DESCRIPTION OF THE INVENTION

According to one aspect of the invention, novel quinoline derivatives of the formula 1

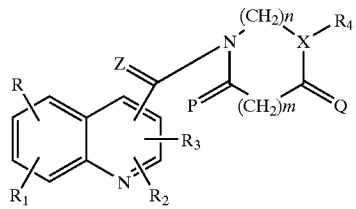

in which

R, $R_1$, $R_2$, $R_3$; can be attached to any of the quinoline carbon atoms $C_2$ to $C_8$, are the same or different and independently of one another denote hydrogen, straight-chain or branched ($C_1$–$C_8$)-alkyl, ($C_3$–$C_1$)-cycloalkyl, straight-chain or branched ($C_1$–$C_8$)-alkylcarbonyl, preferably acetyl, straight-chain or branched ($C_1$–$C_8$)-alkoxy, halogen, aryl-($C_1$–$C_8$)-alkoxy, preferably benzyloxy or phenylethyloxy, nitro, amino, mono-($C_1$–$C_4$) alkylamino, di-($C_1$–$C_4$)-alkylamino, ($C_1$–$C_8$) alkoxycarbonylamino, ($C_1$–$C_6$)-alkoxycarbonylamino-($C_1$–$C_8$)alkyl, cyano, straight-chain or branched cyano-($C_1$–$C_6$)-alkyl, carboxyl, ($C_1$–$C_8$)-alkoxycarbonyl, ($C_1$–$C_4$)-alkyl which is substituted by one or more fluorine atoms, preferably the trifluoromethyl group, carboxy-($C_1$–$C_8$)-alkyl or ($C_1$–$C_8$)-alkoxycarbonyl-($C_1$–$C_6$)-alkyl, ($C_2$–$C_6$)-alkenyl, preferably allyl, ($C_2$–$C_6$)-alkynyl, preferably ethynyl or propargyl, straight-chain or branched cyano-($C_1$–$C_6$)-alkyl, preferably cyanomethyl, aryl, where the aryl radical can be unsubstituted or mono- or polysubstituted by the same or different substituents from the group of halogen, straight-chain or branched ($C_1$–$C_8$)-alkyl, ($C_3$–$C_1$)-cycloalkyl, carboxyl, straightchain or branched ($C_1$–$C_8$)-alkoxycarbonyl, preferably tertbutoxycarbonyl, by trifluoromethyl, hydroxyl, straight-chain or branched ($C_1$–$C_8$)-alkoxy, preferably methoxy or ethoxy, benzyloxy, nitro, amino, mono-($C_1$–$C_4$)-alkylamino, di-($C_1$–$C_4$)-alkylamino, cyano, straight-chain or branched cyano-($C_1$–$C_6$)-alkyl, where additionally R and $R_1$ or $R_2$ and $R_3$ may form a fused aromatic 6-membered ring with the quinoline ring forming an acridine ring which for its part can be substituted at any Catom ring position by the radicals R, $R_1$, $R_2$ and R; having the meanings mentioned above;

Z is oxygen or sulfur, where the radical

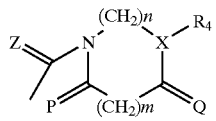

substituted on the quinoline heterocycle can be attached to Catoms $C_2$–$C_8$ of the quinoline ring skeleton;

P, Q independently of one another represent oxygen or in each case two hydrogen atoms (i.e. —$CH_2$—);

X is nitrogen or C—$R_5$, where $R_5$ represents hydrogen or ($C_1$–$C_6$)-alkyl;

n,m independently of one another denotes an integer between 0–3, with the proviso that in the case n=0, X denotes a CR5R6 group where $R_5$ and $R_6$ independently of one another represent hydrogen or ($C_1$–$C_6$)-alkyl and that the nitrogen atom adjacent to the C=Z group is substituted by a hydrogen atom or a ($C_1$–$C_6$)-alkyl group;

$R_4$ or a straight-chain or branched ($C_1$–$C_{20}$)-alkyl radical which can be saturated or unsaturated, with one to three double and/or triple bonds, and which can be unsubstituted or may optionally be substituted at the same or different Catoms by one, two or more aryl, heteroaryl, halogen, cyano, ($C_1$–$C_6$)-alkoxycarbonylamino, ($C_1$–$C_6$)-alkoxy, amino, mono-($C_1$–$C_4$)-alkylamino or di-($C_1$–$C_4$) alkylamino; a ($C_6$–$C_{14}$)-aryl radical, ($C_6$–$C_{14}$)-aryl-($C_1$–$C_4$)-alkyl radical, or a a ($C_2$–$C_{10}$)-heteroaryl or ($C_2$–$C_{10}$)-heteroaryl-($C_1$–$C_4$)-alkyl radical which contains one or more heteroatoms selected from the group of N, 0 and S, where the ($C_1$–$C_4$)-alkyl radical can be unsubstituted or mono- or polysubstituted by the same or different substituents from the group of ($C_1$–$C_6$)-alkyl, halogen or oxo (=O), and where the ($C_6$–$C_{14}$)-aryl or ($C_2$–$C_{10}$)-heteroaryl radical can be unsubstituted or mono- or polysubstituted by the same or different substituents from the group of straight-chain or branched ($C_1$–$C_8$)alkyl, ($C_3$–$C_7$)-cycloalkyl, halogen, cyano, ($C_1$–$C_6$)alkoxycarbonylamino, ($C_1$–$C_6$)-alkoxy, carboxyl, ($C_1$–$C_8$)-alkoxycarbonyl, straight-chain or branched ($C_1$–$C_6$)-alkyl which is substituted by one or more fluorine atoms, preferably trifluoromethyl, hydroxyl, straight-chain or branched ($C_1$–$C_8$)alkoxy, preferably methoxy or ethoxy, where adjacent oxygen atoms may also be linked by ($C_1$–$C_2$)-alkylene groups, preferably by a methylene group, benzyloxy, nitro, amino, mono-($C_1$–$C_4$) alkylamino, di-($C_1$–$C_4$)-alkylamino, aryl, which for its part can be unsubstituted or mono- or polysubstituted by the same or different substituents from the group of straight-chain or branched ($C_1$–$C_8$)-alkyl, ($C_3$–$C_1$)-cycloalkyl, carboxyl, straight-chain or branched ($C_1$–$C_8$)-alkoxycarbonyl, by trifluoromethyl, hydroxyl, straight-chain or branched ($C_1$–$C_8$)-alkoxy, preferably methoxy or ethoxy, benzyloxy, nitro, amino, mono-($C_1$–$C_4$)-alkylamino, di-($C_1$–$C_4$)-alkylamino, cyano, straight-chain or branched cyano-($C_1$–$C_6$)-alkyl;

and their structural isomers and stereoisomers, in particular tautomers, diastereomers and enantiomers, and their pharmaceutically acceptable salts, in particular acid addition salts, are provided.

Thus, for example, the compounds of the formula (1) according to the invention which have one or more centers of chirality and which are present as racemates can be separated by methods known per se into their optical isomers, i.e. enantiomers or diastereomers. The separation can be carried out by column separation on chiral phases or by recrystallization from an optically active solvent or using an optically active acid or base or by derivatization with an optically active reagent, such as, for example, an optically active alcohol, and subsequent removal of the radical.

Furthermore, the quinoline derivatives of the formula (1) according to the invention can be converted into their salts with inorganic or organic acids, in particular, for pharmaceutical use, into their physiologically acceptable salts. Acids which are suitable for this purpose are, for example, hydrochloric acid, hydrobromic acid, sulfuric acid, phosphoric acid, fumaric acid, succinic acid, lactic acid, citric acid, acetic acid, tartaric acid, malic acid, embonic acid, malonic acid, trifluoroacetic acid or maleic acid.

Moreover, the compounds of the formula (1) according to the invention can, if they contain a sufficiently acidic group, such as a carboxyl group, be converted, if desired, into their salts with inorganic or organic bases, in particular, for pharmaceutical use, into their physiologically acceptable salts. Bases which are suitable for this purpose are, for example, sodium hydroxide, potassium hydroxide, calcium hydroxide, lysine, cyclohexylamine, ethanolamine, diethanolamine and triethanolamine.

According to a preferred embodiment, quinoline derivatives of the formula 1 are provided in which R, $R_1$, $R_2$, $R_3$, X, Z, P, Q, n and m have the meanings given above and $R_4$ denotes a straight-chain or branched $(C_1-C_{20})$-alkyl radical which can be saturated or unsaturated, with one to three double and/or triple bonds, and which can be unsubstituted or optionally substituted on the same or different Catoms by one, two or more aryl, heteroaryl, halogen, $(C_1-C_6)$-alkoxy, amino, mono-$(C-C_4)$-alkylamino or di$(C_1-C_4)$-alkylamino;

a phenyl ring or a naphthyl ring, each of which can be unsubstituted or mono- or polysubstituted by the same or different substituents from the group of straight-chain or branched $(C_1-C_8)$-alkyl, $(C_3-C_7)$-cycloalkyl, halogen, carboxyl, $(C_1-C_8)$-alkoxycarbonyl, straightchain or branched $(C_1-C_6)$-alkyl which is substituted by one or more fluorine atoms, preferably trifluoromethyl, hydroxyl, straight-chain or branched $(C_1-C_8)$-alkoxy, preferably methoxy or ethoxy, where adjacent oxygen atoms may also be linked by $(C_1-C_2)$-alkylene groups, preferably a methylene group, benzyloxy, nitro, amino, mono-$(C_1-C_4)$-alkylamino, di-$(C_1-C_4)$-alkylamino, aryl, which for its part can be unsubstituted or mono- or polysubstituted by the same or different substituents from the group of straight-chain or branched $(C_1-C_8)$-alkyl, $(C_3-C_1)$-cycloalkyl, carboxyl, straight-chain or branched $(C_1-C_8)$-alkoxycarbonyl, by trifluoromethyl, hydroxyl, straight-chain or branched $(C_1-C_8)$-alkoxy, preferably methoxy or ethoxy, benzyloxy, nitro, amino, mono-$(C_1-C_4)$-alkylamino, di-$(C_1-C_4)$-alkylamino, cyano, straight-chain or branched cyano-$(C_1-C_6)$alkyl;

a 2-, 4-, 5- or 6-pyrimidinyl radical, or a 2-, 4-, 5- or 6-pyrimidinyl$(C_1-C_4)$-alkyl radical, where the $(C_1-C_4)$-alkyl radical can be unsubstituted or mono- or polysubstituted by the same or different substituents from the group of $(C_1-C_6)$-alkyl, halogen or oxo (=O), and the 2-, 4-, 5- or 6-pyrimidinyl radical can be unsubstituted or mono- to trisubstituted by the same or different substituents from the group of hydrogen, $(C_1-C_6)$-alkyl, halogen, nitro, amino, mono-$(C_1-C_6)$-alkylamino, di-$(C_1-C_6)$-alkylamino, hydroxyl, $(C_1-C_6)$-alkoxy, benzyloxy, carboxyl, $(C_1-C_6)$-alkoxycarbonyl, $(C_1-C_6)$-alkoxycarbonylamino or $(C_1-C_6)$-alkyl which is mono- or polysubstituted by fluorine, preferably trifluoromethyl, $(C_6-C_{10})$-aryl and $(C_6-C_{10})$-aryl-$(C_1-C_6)$-alkyl;

a 3-, 4-, 5- or 6-pyridazinyl radical, or a 3-, 4-, 5- or 6-pyridazinyl$(C_1-C_4)$-alkyl radical, where the $(C_1-C_4)$-alkyl radical can be unsubstituted or mono- or polysubstituted by the same or different substituents from the group of $(C_1-C_6)$-alkyl, halogen or oxo (=O), and the 3-, 4-, 5- or 6-pyridazinyl radical can be unsubstituted or mono- to trisubstituted by the same or different substituents from the group of hydrogen, $(C_1-C_6)$-alkyl, halogen, nitro, amino, mono-$(C_1-C_6)$-alkylamino, di-$(C_1-C_6)$-alkylamino, hydroxyl, $(C_1-C_6)$-alkoxy, benzyloxy, carboxyl, $(C_1-C_6)$-alkoxycarbonyl, $(C_1-C_6)$-alkoxycarbonylamino or $(C_1-C_6)$-alkyl which is mono- or polysubstituted by fluorine, preferably trifluoromethyl, $(C_6-C_{10})$-aryl and $(C_6-C_{10})$-aryl-$(C_1-C_6)$-alkyl;

a 2-, 3-, 5- or 6-pyrazinyl radical, or a 2-, 3-, 5- or 6-pyrazinyl-$(C_1-C_4)$-alkyl radical, where the $(C_1-C_4)$-alkyl radical can be unsubstituted or mono- or polysubstituted by the same or different substituents from the group of $(C_1-C_6)$-alkyl, halogen or oxo (=O), and the 2-, 3-, 5- or 6-pyrazinyl radical can be unsubstituted or mono- to trisubstituted by the same or different substituents from the group of hydrogen, $(C_1-C_6)$-alkyl, halogen, nitro, amino, mono-$(C_1-C_6)$-alkylamino, di-$(C_1-C_6)$-alkylamino, hydroxyl, $(C_1-C_6)$-alkoxy, benzyloxy, carboxyl, $(C_1-C_6)$-alkoxycarbonyl, $(C_1-C_6)$alkoxycarbonylamino or $(C_1-C_6)$-alkyl which is mono- or polysubstituted by fluorine, preferably trifluoromethyl, $(C_6-C_{10})$-aryl and $(C_6-C_{10})$-aryl-$(C_1-C_6)$-alkyl;

a 3-, 4-, 5-, 6-, 7-, or 8-cinnolinyl radical, or a 3-, 4-, 5-, 6-, 7-, or 8cinnolinyl-$(C_1-C_4)$-alkyl radical, where the $(C_1-C_4)$-alkyl radical can be unsubstituted or mono- or polysubstituted by the same or different substituents from the group of $(C_1-C_6)$-alkyl, halogen or oxo (=O), and the 3-, 4-, 5-, 6-, 7-, or 8-cinnolinyl radical can be unsubstituted or mono- to pentasubstituted by the same or different substituents from the group of hydrogen, $(C_1-C_6)$-alkyl, halogen, nitro, amino, mono-$(C_1-C_6)$-alkylamino, di-$(C_1-C_6)$-alkylamino, hydroxyl, $(C_1-C_6)$-alkoxy, benzyloxy, carboxyl, $(C_1-C_6)$-alkoxycarbonyl, $(C_1-C_6)$-alkoxycarbonylamino or $(C_1-C_6)$-,alkyl which is mono- or polysubstituted by fluorine, preferably trifluoromethyl, $(C_6-C_{10})$-aryl and $(C_6-C_{10})$-aryl-$(C_1-C_6)$-alkyl;

a 2-, 4-, 5-, 6-, 7-, or 8-quinazolinyl radical, or a 2-, 4-, 5-, 6-, 7-, or 8-quinazolinyl-$(C_1-C_4)$-alkyl radical, where the $(C_1-C_4)$-alkyl radical can be unsubstituted or mono- or polysubstituted by the same or different substituents from the group of $(C_1-C_6)$-alkyl, halogen or oxo (=O), and the or [sic] 2-, 4-, 5-, 6-, 7-, or 8-quinazolinyl radical can- be unsubstituted or mono- to pentasubstituted by the same or different substituents from the group of hydrogen, $(C_1-C_6)$-alkyl, halogen, nitro, amino, mono-$(C_1-C_6)$.alkylamino, di-$(C_1-C_6)$-alkylamino, hydroxyl, ($C_1$–$C_6$)-alkoxy, benzyloxy, carboxyl, ($C_1$–$C_6$)-alkoxycarbonyl, ($C_1$–$C_6$)-alkoxycarbonylamino or ($C_1$–$C_6$)-alkyl which is mono- or polysubstituted by fluorine, preferably trifluoromethyl, ($C_6$–$C_{10}$)-aryl and ($C_6$–$C_{10}$)-aryl-($C_1$–$C_6$)-alkyl;

a 2-, 3-, 5-, 6-, 7-, or 8-quinoxalinyl radical, or a 2-, 3-, 5-, 6-, 7-, or 8-quinoxalinyl-($C_1$–$C_4$)-alkyl radical, where the ($C_1$–$C_4$)-alkyl radical can be unsubstituted or mono- or polysubstituted by the same or different substituents from the group of ($C_1$–$C_6$)-alkyl, halogen or oxo (=O), and the or [sic] 2-, 3-, 5-, 6-, 7-, or 8-quinoxalinyl radical can be unsubstituted or mono- to pentasubstituted by the same or different substituents from the group of hydrogen, ($C_1$–$C_6$)-alkyl, halogen, nitro, amino, mono-($C_1$–$C_6$)-alkylamino, di-($C_1$–$C_6$)-alkylamino, hydroxyl, ($C_1$–$C_6$)-alkoxy, benzyloxy, carboxyl, ($C_1$–$C_6$)-5 alkoxycarbonyl, ($C_1$–$C_6$)-alkoxycarbonylamino or ($C_1$–$C_6$)-alkyl which is mono- or polysubstituted by fluorine, preferably trifluoromethyl, ($C_6$–$C_{10}$)-aryl and ($C_6$–$C_{10}$)-aryl-($C_1$–$C_6$)-alkyl;

a 1-, 4-, 5-, 6-, 7-, or 8-phthalazinyl radical, or a 1-, 4-, 5-, 6-, 7-, or 8-phthalazinyl-($C_1$–$C_4$)-alkyl radical, where the ($C_1$–$C_4$)-alkyl radical can be unsubstituted or mono- or polysubstituted by the same or different substituents from the group of ($C_1$–$C_6$)-alkyl, halogen or oxo (=O), and the or [sic] 1-, 4-, 5-, 6-, 7-, or 8-phthalazinyl radical can be unsubstituted or mono- to pentasubstituted by the same or different substituents from the group of hydrogen, ($C_1$–$C_6$)-alkyl, halogen, nitro, amino, mono-($C_1$–$C_6$)-alkylamino, di-($C_1$–$C_6$)alkylamino, hydroxyl, ($C_1$–$C_6$)-alkoxy, benzyloxy, carboxyl, ($C_1$–$C_6$)alkoxycarbonyl, ($C_1$–$C_6$)-alkoxycarbonylamino or ($C_1$–$C_6$)-alkyl which is mono- or polysubstituted by fluorine, preferably trifluoromethyl, ($C_6$–$C_{10}$)-aryl and ($C_6$–$C_{10}$)-aryl-($C_1$–$C_6$)-alkyl;

a 2-, 3-, 4-, 5-, 6-, 7- or 8-quinolyl radical, or a 2-, 3-, 4-, 5-, 6-, 7 or 8-quinolyl-($C_1$–$C_4$)-alkyl radical, where the ($C_1$–$C_4$)-alkyl radical can be unsubstituted or mono- or polysubstituted by the same or different substituents from the group of ($C_1$–$C_6$)-alkyl, halogen or oxo (=O), and the 2-, 3-, 4-, 5-, 6-, 7- or 8-quinolyl radical can be unsubstituted or -mono- to hexasubstituted by the same or different substituents from the group of hydrogen, ($C_1$–$C_6$)-alkyl, preferably methyl, particularly preferably 2-methyl, halogen, nitro, amino, mono-($C_1$–$C_6$)-alkylamino, di-($C_1$–$C_6$)-alkylamino, hydroxyl, ($C_1$–$C_6$)-alkoxy, benzyloxy, carboxyl, ($C_1$–$C_6$)-alkoxycarbonyl, ($C_1$–$C_6$)-alkoxycarbonylamino or ($C_1$–$C_6$)-alkyl which is mono- or polysubstituted by fluorine, preferably trifluoromethyl, ($C_6$–$C_{10}$)-aryl 10 and ($C_6$–$C_{10}$)-aryl-($C_1$–$C_6$)-alkyl;

a 1-, 3-, 4-, 5-, 6-, 7- or 8-isoquinolyl radical, or a 1-, 3-, 4-, 5-, 6-, 7 or 8-isoquinolyl-($C_1$–$C_4$)-alkyl radical, where the ($C_1$–$C_4$)-alkyl radical can be unsubstituted or mono- or polysubstituted by the same or different substituents from the group of ($C_1$–$C_6$)-alkyl, halogen or oxo (=O), and the 1-, 3-, 4-, 5-, 6-, 7- or 8-isoquinolyl radical can be unsubstituted or mono- to hexasubstituted by the same or different substituents from the group of hydrogen, ($C_1$–$C_6$)-alkyl, halogen, nitro, amino, mono-($C_1$–$C_6$)-alkylamino, di-($C_1$–$C_6$)-alkylamino, hydroxyl, ($C_1$–$C_6$)-alkoxy, benzyloxy, carboxyl, ($C_1$–$C_6$) alkoxycarbonyl, ($C_1$–$C_6$)-alkoxycarbonylamino or ($C_1$–$C_6$)-alkyl which is mono- or polysubstituted by fluorine, preferably trifluoromethyl, ($C_6$–$C_{10}$)-aryl and ($C_6$–$C_{10}$)-aryl-($C_1$–$C_6$)-alkyl;

a 2-, 6-, 8- or 9-[9H]-purinyl radical, or a 2-, 6-, 8- or 9-[9H]purinyl-($C_4$–$C_4$)-alkyl radical, where the ($C_1$–$C_4$)-alkyl radical can be unsubstituted or mono- or polysubstituted by the same or different substituents from the group of ($C_1$–$C_6$)-alkyl, halogen or-oxo (=O), and the 2-, 6-, 8- or 9-[9H]-purinyl radical can be unsubstituted or mono- to trisubstituted by the same or different substituents from the group of hydrogen, ($C_1$–$C_6$)-alkyl, halogen, nitro, amino, mono-($C_1$–$C_6$)-alkylamino, di-($C_1$–$C_6$)-alkylamino, hydroxyl, ($C_1$–$C_6$)-alkoxy, benzyloxy, carboxyl, ($C_1$–$C_6$)-alkoxycarbonyl, ($C_1$–$C_6$) alkoxycarbonylamino or ($C_1$–$C_6$)-alkyl which is mono- or polysubstituted by fluorine, preferably trifluoromethyl, ($C_6$–$C_{10}$)-aryl and ($C_6$–$C_{10}$)-aryl-($C_1$–$C_6$)-alkyl;

a 2-, 6-, 7- or 8-[7H]-purinyl radical, or a 2-, 6-, 7- or 8-[7H]purinyl-($C_1$–$C_4$)-alkyl radical, where the ($C_1$–$C_4$)-alkyl radical can be unsubstituted or mono- or polysubstituted by the same or different substituents from the group of ($C_1$–$C_6$)-alkyl, halogen or oxo (=O), and the 2-, 6-, 7- or 8-[7H]-purinyl radical can be unsubstituted or mono- to trisubstituted by the same or different substituents from the group of hydrogen, ($C_1$–$C_6$)-alkyl, halogen, nitro, amino, mono-($C_1$–$C_6$)-alkylamino, di-($C_1$–$C_6$)-alkylamino, hydroxyl, ($C_1$–$C_6$)-alkoxy, benzyloxy, carboxyl, ($C_1$–$C_6$)-alkoxycarbonyl, ($C_1$–$C_6$ alkoxycarbonylamino or ($C_1$–$C_6$)-alkyl which is mono- or polysubstituted by fluorine, preferably trifluoromethyl, ($C_6$–$C_{10}$)-aryl and ($C_6$–$C_{10}$)-aryl-($C_1$–$C_6$)-alkyl;

a 1-, 2-, 3-, 4-, 5-, 6-, 7-, 8- or 9-acridinyl radical, or a 1-, 2-, 3-, 4-, 5-, 6-, 7-, 8- or 9-acridinyl-($C_1$–$C_4$)-alkyl radical, where the ($C_1$–$C_6$)-alkyl radical can be unsubstituted or mono- or polysubstituted by the same or different substituents from the group of ($C_1$–$C_6$)-alkyl, halogen or oxo (=O), and the 1-, 2-, 3-, 4-, 5-, 6-, 7-, 8- or 9acridinyl radical can be unsubstituted or mono- to octasubstituted by the same or different substituents from the group of hydrogen, ($C_1$–$C_6$)-alkyl, halogen, nitro, amino, mono-($C_1$–$C_6$)-alkylamino, di-($C_1$–$C_6$)-alkylamino, hydroxyl, ($C_1$–$C_6$)-alkoxy, benzyloxy, carboxyl, ($C_1$–$C_6$)-alkoxycarbonyl, ($C_1$–$C_6$)-alkoxycarbonylamino or ($C_1$–$C_6$)-alkyl which is mono- or polysubstituted by fluorine, preferably trifluoromethyl, ($C_6$–$C_{10}$)-aryl and ($C_6$–$C_{10}$)-aryl-($C_1$–$C_6$)-alkyl;

a 1-, 2-, 3-, 4-, 5-, 6-, 7-, 8- or 9-phenanthridinyl radical, or a 1-, 2-, 3-, 4-, 5-, 6-, 7-, 8- or 9-phenanthridinyl-($C_1$–$C_6$)-alkyl radical, where the ($C_1$–$C_6$)-alkyl radical can be unsubstituted or mono- or polysubstituted by the same or different substituents from the group of hydrogen, ($C_1$–$C_6$)-alkyl, halogen or oxo (=O), and the 1-, 2-, 3-, 4-, 5-, 6-, 7-, 8- or 9-phenanthridinyl radical can be unsubstituted or mono- to octasubstituted by the same or different substituents from the group of ($C_1$–$C_6$)-alkyl, halogen, nitro, amino, mono-($C_1$–$C_6$)-alkylamino, di-($C_1$–$C_6$)-alkylamino, hydroxyl, ($C_1$–$C_6$)-alkoxy, ($C_6$–$C_{10}$)-aryl-($C_1$–$C_6$)-alkoxy, preferably benzyloxy, carboxyl, ($C_1$–$C_6$)-alkoxycarbonyl, ($C_1$–$C_6$)-alkoxycarbonylamino or ($C_1$–$C_6$)-alkyl which is mono- or polysubstituted by fluorine, preferably trifluoromethyl, ($C_6$–$C_{10}$)-aryl and ($C_6$–$C_{10}$)-aryl-($C_1$–$C_6$)-alkyl;

a 2-, 3-, 4-, 5- or 6-pyridyl radical where the 2-, 3-, 4-, 5- or 6pyridyl radical can be unsubstituted or mono- to tetrasubstituted by the same or different substituents from the group of hydrogen, ($C_1$–$C_6$)-alkyl, halogen, nitro, amino, mono-$(C_1-C_6)$-alkylamino, di-$(C_1-C_6)$-alkylamino, hydroxyl, $(C_1-C_6)$-alkoxy, benzyloxy, carboxyl, $(C_1-C_6)$-alkoxycarbonyl, $(C_1-C_6)$-alkoxycarbonylamino or $(C_1-C_6)$-alkyl which is mono- or polysubstituted by fluorine, preferably trifluoromethyl, $(C_6-C_{10})$-aryl and $(C_6-C_{10})$-aryl-$(C_1-C_6)$-alkyl;

a 2-, 3-, 4-, 5- or 6-pyridinyl-$(C_1-C_6)$-alkyl radical, where the $(C_1-C_6)$-alkyl radical can be unsubstituted or mono- or polysubstituted by the same or different substituents from the group of $(C_1-C_6)$alkyl, halogen or oxo (=O), and the 2-, 3-, 4-, 5- or 6-pyridinyl radical can be unsubstituted or mono- to tetrasubstituted by the same or different substituents from the group of hydrogen, $(C_1-C_6)$-alkyl, halogen, nitro, amino, mono-$(C_1-C_6)$-alkylamino, di-$(C_1-C_6)$ alkylamino, hydroxyl, $(C_1-C_6)$-alkoxy, benzyloxy, carboxyl, $(C_1-C_6)$-alkoxycarbonyl, $(C_1-C_6)$-alkoxycarbonylamino or $(C_1-C_6)$-alkyl which is mono- or polysubstituted by fluorine, preferably trifluoromethyl, $(C_6-C_{10})$-aryl and $(C_6-C_{10})$-aryl-$(C_1-C_6)$-alkyl;

a 2-, 3-, 4- or 5-thienyl radical, or a 2-, 3-, 4- or 5-thienyl-$(C_1-C_6)$ alkyl radical, where the $(C_1-C_6)$-alkyl radical can be unsubstituted or mono- or polysubstituted by the same or different substituents from the group of $(C_1-C_6)$-alkyl, halogen or oxo (=O), and the 2-, 3-, 4- or 5-thienyl radical can be unsubstituted or mono- to trisubstituted by the same or different substituents from the group of hydrogen, $(C_1-C_6)$-alkyl, halogen, nitro, amino, mono-$(C_1-C_6)$-alkylamino, di-$(C_1-C_6)$-alkylamino, hydroxyl, $(C_1-C_6)$-alkoxy, benzyloxy, carboxyl, $(C_1-C_6)$-alkoxycarbonyl, $(C_1-C_6)$-alkoxycarbonylamino or $(C_1-C_6)$-alkyl which is mono- or polysubstituted by fluorine, preferably trifluoromethyl, $(C_6-C_{10})$-aryl and $(C_6-C_{10})$-aryl-$(C_1-C_6)$-alkyl;

a 2-, 4-, or 5-thiazolyl radical, or a 2-, 4-, or 5-thiazolyl-$(C_1-C_6)$-alkyl radical, where the $(C_1-C_6)$-alkyl radical can be unsubstituted or mono- or polysubstituted by the same or different substituents from the group of $(C_1-C_6)$-alkyl, halogen or oxo (=O), and the 2-, 4-, or 5thiazolyl radical can be unsubstituted or mono- or disubstituted by the same or different substituents from the group of hydrogen, $(C_1-C_6)$-alkyl, halogen, nitro, amino, mono-$(C_1-C_6)$-alkylamino, di-$(C_1-C_6)$-alkylamino, hydroxyl, $(C_1-C_6)$-alkoxy, benzyloxy, carboxyl, $(C_1-C_6)$-alkoxycarbonyl, $(C_1-C_6)$-alkoxycarbonylamino or $(C_1-C_6)$-alkyl which is mono- or polysubstituted by fluorine, preferably trifluoromethyl, $(C_6-C_{10})$-aryl and $(C_6-C_{10})$-aryl-$(C_1-C_6)$-alkyl;

a 3-, 4-, or 5-isothiazolyl radical, or a 3-, 4-, or 5-isothiazolyl-$(C_1-C_6)$-alkyl radical, where the $(C_1-C_6)$-alkyl radical can be unsubstituted or mono- or polysubstituted by the same or different substituents from the group of $(C_1-C_6)$-alkyl, halogen or oxo (=O), and the 3-, 4-, or 5-isothiazolyl radical can be unsubstituted or mono- or disubstituted by the same or different substituents from the group of hydrogen, $(C_1-C_6)$-alkyl, halogen, nitro, amino, mono-$(C_1-C_6)$-alkylamino, di-$(C_1-C_6)$-alkylamino, hydroxyl, $(C_1-C_6)$-alkoxy, benzyloxy, carboxyl, $(C_1-C_6)$-alkoxycarbonyl, $(C_1-C_6)$-alkoxycarbonylamino or $(C_1-C_6)$-alkyl which is mono- or polysubstituted by fluorine, preferably trifluoromethyl, $(C_6-C_{10})$-aryl and $(C_6-C_{10})$-aryl-$(C_1-C_6)$-alkyl;

a 2-, 4-, 5-, 6-, or 7-benzothiazolyl radical, or a 2-, 4-, 5-, 6-, or 7 benzothiazolyl-$(C_1-C_6)$-alkyl radical, where the $(C_1-C_6)$-alkyl radical can be unsubstituted or mono- or polysubstituted by the same or different substituents from the group of $(C_1-C_6)$-alkyl, halogen or oxo (=O), and the 2-, 4-, 5-, 6-, or 7-benzothiazolyl radical can be unsubstituted or mono- to tetrasubstituted by the same or different substituents from the group of hydrogen, $(C_1-C_6)$-alkyl, halogen, nitro, amino, mono-$(C_1-C_6)$-alkylamino, di-$(C_1-C_6)$-alkylamino, hydroxyl, $(C_1-C_6)$-alkoxy, benzyloxy, carboxyl, $(C_1-C_6)$-alkoxycarbonyl, $(C_1-C_6)$-alkoxycarbonylamino or $(C_1-C_6)$-alkyl which is mono- or poly- substituted by fluorine, preferably trifluoromethyl, $(C_6-C_{10})$-aryl-and $(C_6-C_{10})$-aryl-$(C_1-C_6)$-alkyl;

a 1-, 2-, 4-, or 5-imidazolyl radical, or a 1-, 2-, 4-, or 5-imidazolyl$(C_1-C_6)$-alkyl radical, where the $(C_1-C_6)$-alkyl radical can be unsubstituted or mono- or polysubstituted by the same or different substituents from the group of $(C_1-C_6)$-alkyl, halogen or oxo (=O), and the 1-, 2-, 4-, or 5-imidazolyl radical can be unsubstituted or mono- to trisubstituted by the same or different substituents from the group of hydrogen, $(C_1-C_6)$-alkyl, halogen, nitro, amino, mono-$(C_1-C_6)$-alkylamino, di-$(C_1-C_6)$-alkylamino, hydroxyl, $(C_1-C_6)$-alkoxy, benzyloxy, carboxyl, $(C_1-C_6)$-alkoxycarbonyl, $(C_1-C_6)$-alkoxycarbonylamino or $(C_1-C_6)$-alkyl which is mono- or polysubstituted by fluorine, preferably trifluoromethyl, $(C_6-C_{10})$-aryl and $(C_6-C_{10})$-aryl-$(C_1-C_6)$-alkyl;

a 1-, 3-, 4-, or 5-pyrazolyl radical, or a 1-, 3-, 4- or 5-pyrazolyl-$(C_1-C_6)$-alkyl radical, where the $(C_1-C_6)$-alkyl radical can be unsubstituted or mono- or polysubstituted by the same or different substituents from the group of $(C_1-C_6)$-alkyl, halogen or oxo (=O), and the 1-, 3-, 4- or 5-pyrazolyl radical can be unsubstituted or mono- to trisubstituted by the same or different substituents from the group of hydrogen, $(C_1-C_6)$-alkyl, halogen, nitro, amino, mono-$(C_1-C_6)$-alkylamino, di-$(C_1-C_6)$-alkylamino, hydroxyl, $(C_1-C_6)$-alkoxy, benzyloxy, carboxyl, $(C_1-C_6)$-alkoxycarbonyl, $(C_1-C_6)$-alkoxycarbonylamino or $(C_1-C_6)$-alkyl which is mono- or polysubstituted by fluorine, preferably trifluoromethyl, $(C_6-C_{10})$-aryl and $(C_6-C_{10})$-aryl-$(C_1-C_6)$-alkyl;

a 1-, 2-, 3-, 4-, or 5-pyrrolyl radical, or a 1-, 2-, 3-, 4-, or 5-pyrrolyl$(C_1-C_6)$-alkyl radical, where the $(C_1-C_6)$-alkyl radical can be unsubstituted or mono- or polysubstituted by the same or different substituents from the group of $(C_1-C_6)$-alkyl, halogen or oxo (=O), and the 1-, 2-, 3-, 4- or 5-pyrrolyl radical can be unsubstituted or mono- to tetrasubstituted by the same or different substituents from the group of hydrogen, $(C_1-C_6)$-alkyl, halogen, nitro, amino, mono$(C_1-C_6)$-alkylamino, di-$(C_1-C_6)$-alkylamino, hydroxyl, $(C_1-C_6)$-alkoxy, benzyloxy, carboxyl, $(C_1-C_6)$-alkoxycarbonyl, $(C_1-C_6)$alkoxycarbonylamino or $(C_1-C_6)$-alkyl which is mono- or polysubstituted by fluorine, preferably trifluoromethyl, $(C_6-C_{10})$-aryl and $(C_6-C_{10})$-aryl-$(C_1-C_6)$-alkyl;

a 1-, 3-, or 5-[1.2.4]-triazolyl radical, or a 1-, 3-, or 5-[1.2.4]-triazolyl-$(C_1-C_6)$-alkyl radical, where the $(C_1-C_6)$-alkyl radical can be unsubstituted or mono- or polysubstituted by the same or different substituents from the group of hydrogen, $(C_1-C_6)$-alkyl, halogen or oxo (=O), and the 1-, 3-, or 5-[1.2.4]-triazolyl radical can be unsubstituted or mono- or disubstituted by the same or different substituents from the group of $(C_1-C_6)$-alkyl, halogen, nitro, amino, mono-$(C_1-C_6)$-alkylamino, di-$(C_1-C_6)$-alkylamino, hydroxyl, $(C_1-C_6)$-alkoxy, benzyloxy, carboxyl, $(C_1-C_6)$-alkoxycarbonyl, $(C_1-C_6)$ alkoxycarbonylamino or $(C_1-C_6)$-alkyl which is mono- or polysubstituted by fluorine, preferably trifluoromethyl, $(C_6-C_{10})$-aryl and $(C_6-C_{10})$-aryl-$(C_1-C_6)$-alkyl;

a 1-, 4-, or 5-[1.2.3]-triazolyl radical, or a 1-, 4-, or 5-[1.2.3]triazolyl-$(C_1-C_6)$-alkyl radical, where the $(C_1-C_6)$-alkyl radical can be unsubstituted or mono- or polysubstituted by the same or different substituents from the group of $(C_1-C_6)$-alkyl, halogen or oxo (=O), and the 1-, 4-, or 5-[1.2.3]-triazolyl radical can be unsubstituted or mono- or disubstituted by the same or different substituents from the group of hydrogen, $(C_1-C_6)$-alkyl, halogen, nitro, amino, mono-$(C_1-C_6)$-alkylamino, di-$(C_1-C_6)$-alkylamino, hydroxyl, $(C_1-C_6)$-alkoxy, benzyloxy, carboxyl, $(C_1-C_6)$-alkoxycarbonyl, $(C_1-C_6)$alkoxycarbonylamino or $(C_1-C_6)$-alkyl which is mono- or polysubstituted by fluorine, preferably trifluoromethyl, $(C_6-C_{10})$-aryl and $(C_6-C_{10})$-aryl-$(C_1-C_6)$-alkyl;

a 1- or 5-[1H]-tetrazolyl radical, or a 1-, or 5-[1H]-tetrazolyl-$(C_1-C_6)$-alkyl radical, where the $(C_1-C_6)$-alkyl radical can be unsubstituted or mono- or polysubstituted by the same or different substituents from the group of $(C_1-C_6)$-alkyl, halogen or oxo (=O), and the 1-, or 5-[1H]-tetrazolyl radical can be unsubstituted or substituted by hydrogen, $(C_1-C_6)$-alkyl, halogen, nitro, amino, mono-$(C_1-C_6)$-alkylamino, di-$(C_1-C_6)$-alkylamino, hydroxyl, $(C_1-C_6)$ alkoxy, benzyloxy, carboxyl, $(C_1-C_6)$-alkoxycarbonyl, $(C_1-C_6)$-alkoxycarbonylamino or $(C_1-C_6)$-alkyl which is mono- or polysubstituted by fluorine, preferably trifluoromethyl, $(C_6-C_{10})$-aryl and $(C_6-C_{10})$-aryl-$(C_1-C_6)$-alkyl;

a 2- or 5-[2H]-tetrazoyl radical, or a 2- or 5-[2H]-tetrazolyl-$(C_1-C_6)$ alkyl radical, where the $(C_1-C_6)$-alkyl radical can be unsubstituted or mono- or polysubstituted by the same or different substituents from the group of $(C_1-C_6)$-alkyl, halogen or oxo (=O), and the 2- or 5[2H]-tetrazolyl radical can be unsubstituted or substituted by hydrogen, $(C_1-C_6)$-alkyl, halogen, nitro, amino, mono-$(C_1-C_6)$ alkylamino, di-$(C_1-C_6)$-alkylamino, hydroxyl, $(C_1-C_6)$-alkoxy, benzyloxy, carboxyl, $(C_1-C_6)$-alkoxycarbonyl, $(C_1-C_6)$alkoxycarbonylamino or $(C_1-C_6)$-alkyl which is mono- or polysubstituted by fluorine, preferably trifluoromethyl, $(C_6-C_{10})$-aryl and $(C_6-C_{10})$-aryl-$(C_1-C_6)$-alkyl;

a 2-, 4-, or 6-[1.3.5]-triazinyl radical, or a 2-, 4-, or 6-[1.3.5]triazinyl-$(C_1-C_6)$-alkyl radical, where the $(C_1-C_6)$-alkyl radical can be unsubstituted or mono- or polysubstituted by the same or different substituents from the group of hydrogen, $(C_1-C_6)$-alkyl, halogen or oxo (=O), and the 2-, 4-, or 6-[1.3.5]-triazinyl radical can be unsubstituted or mono- or disubstituted by the same or different substituents from the group of hydrogen, $(C_1-C_6)$-alkyl, halogen, nitro, amino, mono-$(C_1-C_6)$-alkylamino, di-$(C_1-C_6)$-alkylamino, hydroxyl, $(C_1-C_6)$-alkoxy, benzyloxy, carboxyl, $(C_1-C_6)$-alkoxycarbonyl, $(C_1-C_6)$-alkoxycarbonylamino or $(C_1-C_6)$-alkyl which is mono- or polysubstituted by fluorine, preferably trifluoromethyl, $(C_6-C_{10})$-aryl and $(C_6-C_{10})$-aryl-$(C_1-C_6)$-alkyl;

a 2-, 4-, or 5-oxazolyl radical, or a 2-, 4-, or 5-oxazolyl-$(C_1-C_6)$-alkyl radical, where the $(C_1-C_6)$-alkyl radical can be unsubstituted or mono- or polysubstituted by the same or different substituents from the group of $(C_1-C_6)$-alkyl, halogen or oxo (=O), and the 2-, 4-, or 5-oxazolyl radical can be unsubstituted or mono- or disubstituted by the same or different substituents from the group of hydrogen, $(C_1-C_6)$-alkyl, halogen, nitro, amino, mono-$(C_1-C_6)$-alkylamino, di-$(C_1-C_6)$-alkylamino, hydroxyl, $(C_1-C_6)$-alkoxy, benzyloxy, carboxyl, $(C_1-C_6)$-alkoxycarbonyl, $(C_1-C_6)$-alkoxycarbonylamino or $(C_1-C_6)$-alkyl which is mono- or polysubstituted by fluorine, preferably trifluoromethyl, $(C_6-C_1)$-aryl and $(C_6-C_{10})$-aryl-$(C_1-C_6)$-alkyl;

a 3-, 4-, or 5-isoxazolyl radical, or a 3-, 4-, or 5-isoxazolyl-$(C_1-C_6)$alkyl radical, where the $(C_1-C_6)$-alkyl radical can be unsubstituted or mono- or polysubstituted by the same or different substituents from the group of $(C_1-C_6)$-alkyl, halogen or oxo (=O), and the 3-, 4-, or 5-isoxazolyl radical can be unsubstituted or mono- or disubstituted by the same or different substituents from the group of hydrogen, $(C_1-C_6)$-alkyl, halogen, nitro, amino, mono-$(C_1-C_6)$-alkylamino, di$(C_1-C_6)$-alkylamino, hydroxyl, $(C_1-C_6)$-alkoxy, benzyloxy, carboxyl, $(C_1-C_6)$-alkoxycarbonyl, $(C_1-C_6)$-alkoxycarbonylamino or $(C_1-C_6)$-alkyl which is mono- or polysubstituted by fluorine, preferably trifluoromethyl, $(C_6-C_{10})$-aryl and $(C_6-C_{10})$-aryl-$(C_1-C_6)$-alkyl;

a 1-, 2-, 3-, 4-, 5-, 6- or 7-indolyl radical, or a 1-, 2-, 3-, 4-, 5-, 6- or 7-indolyl-$(C_1-C_6)$-alkyl radical, where the $(C_1-C_6)$-alkyl radical can be unsubstituted or mono- or polysubstituted by the same or different substituents from the group of $(C_1-C_6)$-alkyl, halogen or oxo (=O), and the 1-, 2-, 3-, 4-, 5-, 6- or 7-indolyl radical can be unsubstituted or mono- to hexasubstituted by the same or different substituents from the group of hydrogen, $(C_1-C_6)$-alkyl, halogen, nitro, amino, mono-$(C_1-C_6)$-alkylamino, di-$(C_1-C_6)$-alkylamino, hydroxyl, $(C_1-C_6)$-alkoxy, benzyloxy, carboxyl, $(C_1-C_6)$ alkoxycarbonyl, $(C_1-C_6)$-alkoxycarbonylamino or $(C_1-C_6)$-alkyl which is mono- or polysubstituted by fluorine, preferably trifluoromethyl, $(C_6-C_{10})$-aryl and $(C_6-C_{10})$-aryl-$(C_1-C_6)$-alkyl and the isomers, in particular tautomers, diastereomers and enantiomers, and the pharmaceutically acceptable salts, in particular acid addition salts, thereof.

According to a further embodiment, quinoline derivatives of the formula (1) are provided which are characterized in that R, R, $R_2$, $R_3$, X, Z, P, Q, n and m have the meanings given above and R4 represents phenyl which is unsubstituted or substituted by one to five the same or different $(C_1-C_6)$-alkoxy groups, where adjacent oxygen atoms may also be linked by $(C_1-C_2)$-alkylene groups. According to a further embodiment, quinoline derivatives of the formula (1) are provided which are characterized in that R, R, $R_2$, $R_3$, X, Z, P, Q, n and m have the meanings given above and $R_4$ represents 3,5 dimethoxyphenyl.

According to a further embodiment, quinoline derivatives of the formula (1) are provided which are characterized in that $R_4$ has the meanings given above, R, $R_1$, $R_2$, $R_3$ each represent a hydrogen atom, Z represents an oxygen atom and X represents a nitrogen atom, P and Q each represent two hydrogen atoms (i.e. —$CH_2$—), m is zero and n is the integer 2.

According to a further embodiment, quinoline derivatives of the 20 formula (1) are provided which are characterized in that R, $R_1$, $R_2$, $R_3$ each represent a hydrogen atom, Z represents an oxygen atom, X represents a nitrogen atom, P and Q each represent two hydrogen atoms (i.e. —CH2-), m is zero, n represents the integer 2 and $R_4$ represents a 3,5-dimethoxyphenyl radical.

According to a further aspect of the invention, a process for preparing quinoline derivatives of the formula (1) is provided which is characterized in that a quinoline carboxylic acid of the formula (2)

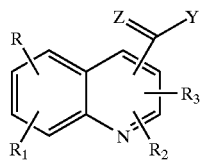

in which R, $R_1$, $R_2$, $R_3$ have the meanings given above, Z denotes an oxygen or sulfur atom and Y represents a leaving group such as halogen, hydroxyl, $(C_1-C_6)$-alkoxy, preferably methoxy or ethoxy, -0-tosyl, -0mesyl or imidazolyl, is reacted with an amine of the formula (3)

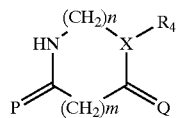

in which $R_4$, X, P, Q, m and n are as defined above, using, if appropriate, diluents and auxiliaries, and the desired quinoline derivatives are formed.

Synthesis Route:

The compounds of the formula 1 can be obtained according to Scheme 1 below:

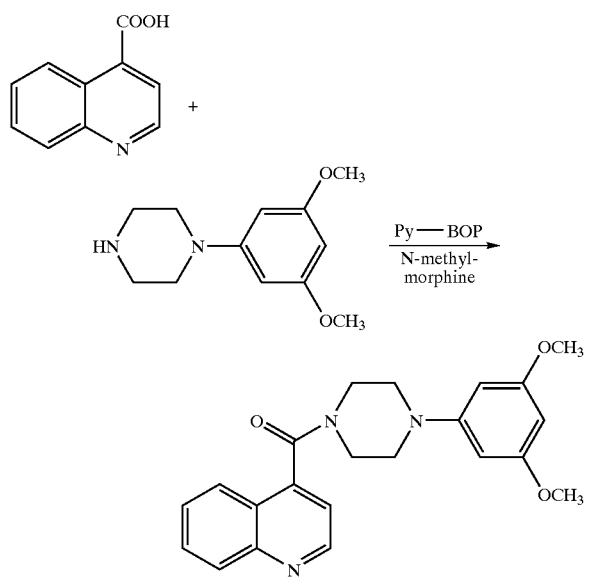

The starting materials (2) and (3) are either commercially available or can be prepared by procedures known per se. The starting materials (2) and (3) are useful intermediates for preparing the quinoline derivatives of the formula (1) according to the invention.

The solvents and auxiliaries to be used, if appropriate, and the reaction parameters to be used, such as reaction temperature and reaction time, are known to the person skilled in the art owing to his expert knowledge.

The quinoline derivatives of the formula (1) according to the invention are suitable as medicaments, in particular as antitumor agents, for treating mammals, in particular man, but also domestic animals such as horses, cattle, dogs, cats, hares, sheep, poultry and the like.

According to a further aspect of the invention, a method for controlling tumors in mammals, in particular man, is provided which is characterized in that at least one quinoline derivative of the formula (1) is administered to a mammal in an amount effective for the treatment of the tumor. The therapeutically effective dose of the quinoline derivative according to the invention in question which is to be administered for the treatment depends inter alia on the nature and the stage of the oncosis, the age and the sex of the patient, the type of administration and the duration of the treatment. Administration can take place orally, rectally, buccally (for example sublingually), parenterally (for example subcutaneously, intramuscularly, intradermally or intravenously), topically or transdermally.

According to a further aspect of the invention, medicaments for the treatment of tumors are provided which are characterized in that they comprise, as active ingredient, at least one quinoline derivative according to any of claims 1 to 4 or a pharmaceutically acceptable salt thereof, if appropriate together with customary pharmaceutically acceptable auxiliaries, additives and carriers. These can be solid, semisolid, liquid or aerosol preparations. Suitable solid preparations are, for example, capsules, powders, granules, tablets. Suitable semisolid preparations are, for example, ointments, creams, gels, pastes, suspensions, oil-in-water and water-in-oil emulsions. Suitable liquid preparations are, for example, sterile aqueous preparations for parenteral administration which are isotonic with the blood of the patient.

The invention is to be illustrated in more detail by the example below, without being restricted to the example.

1-(3,5-dimethoxyphenyl)-4-(4-quinolyl-carbonyl) piperazine 2 g (11.5 mmol) of quinoline-4-carboxylic acid were suspended in 80 ml of DMF. With stirring, 1.74 g (17.2 mmol) of N-methylmorpholine and then a solution of 8.95 g (17.2 mmol) of Py-BOP (1-benzotriazolyltripyrrolidinophosphonium hexafluorophosphate) and 2.56 g (11.5 mmol) of 1-(3,5-dimethoxyphenyl)piperazine in 25 ml of DMF were added to this mixture. The mixture was stirred at RT for 12 h, the DMF was distilled off under reduced pressure and the residue was purified on a silica gel column (Kieselgel 60, from Merck AG, Darmstadt) using the mobile phase dichloromethane/methanol/25 percent ammonia (90:10:1 v/v/v).

Yield: 3.4 g (78.3% of theory)

m.p.: 146–148° C.

1. Antiproliferative Action in Various Tumor Cell Lines

In a proliferation test, the antiproliferative activity of the substance D-43411 was examined using established tumor cell lines. In the test used, the cellular dehydrogenation activity is determined, which makes it possible to determine the vitality of the cell and, indirectly, the cell count. The cell lines used are the human cervical carcinoma cell lines KB/HeLa (ATCC/CCL17), the murine lymphocyte leukaemia L1210 (ATCC CCL-219), the human breast adenocarcinoma line MCF7/ATCC HTB22) and the ovary adenocarcinoma line SKOV-3 (ATCC HTB77). These are established cell lines which are very well characterized and were obtained from ATCC and cultured.

The results shown in Tab. 1 demonstrate the highly potent antiproliferative action of D-43411 in the cell lines SKOV-3, L-1210 and HeLa/KB. Owing to the particularly slow growth of the MCF7 line, the effect of D-43411 in the test period of 48 h is only small (18% inhibition at 3.16_g/ml; thus stated as >3.16).

Tab. 1

In-vitro cytotoxicity in tumor cell lines (values determined from 5 substance concentrations)

| D number | Structure | MW | XTT-Assay IC$_{50}$ [μg/ml] | | | |
|---|---|---|---|---|---|---|
| | | | SKOV-3 | L1210 | KB/HeLa | MCF7 |
| D-43411 | 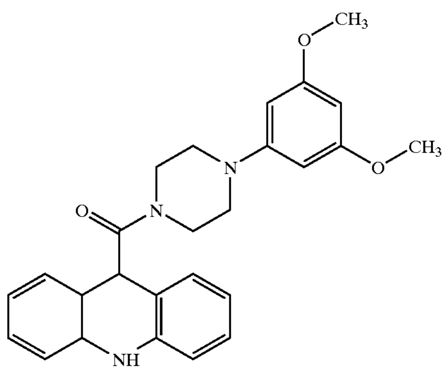 | 429 | <0.0003 | <0.0003 | <0.0003 | >3.16 |

2. Method
XTT Test for Cellular Dehydrogenase Activity

The adherently growing tumor cell lines HeLa/KB, SKOV-3 and MCF7 and the L1210 leukaemia line, which grows in suspension, were cultivated under standard conditions in an incubator with gas inlet at 37° C., 5% $CO_2$ and 95% atmospheric humidity. On Test Day 1, the adherent cells are detached using trypsine/EDTA and pelleted by centrifugation. The cell pellet is then resuspended in RPMI culture medium at the appropriate cell count and transferred to a 96-well microtitre plate. The plates are then cultivated overnight in the incubator with gas inlet. The test substances are made up as stock solutions in DMSO and, on Test Day 2, diluted with culture medium to the desired concentrations. The substances in the culture medium are then added to the cells and incubated in the incubator with gas inlet for 45 h. Cells which have not been treated with test substance serve as control.

For the XTT assay, 1 mg/ml of XTT (sodium 3'-[1-(phenylaminocarbonyl)-3,4-tetrazolium]-bis(4-methoxy-6-nitro)benzenesulfonic acid) is dissolved in RPMI-1640 medium without Phenol Red. Additionally, a 0.383 mg/ml solution of PMS (N-methyldibenzopyrazine methyl sulfate) in phosphate-buffered saline (PBS) is prepared. On Test Day 4, 75 _1/well of the XTT-PMS mixture are pipetted onto the cell plates, which by now have been incubated with the test substances for 45 h. To this end, the XTT solution is mixed with the PMS solution in a ratio of 50:1 (v/v) shortly before use. The cell plates are then incubated in the incubator with gas inlet for a further 3 h, and the optical density ($OD_{490nm}$) is determined in a photometer.

Using the $OD_{490nm}$ obtained, the inhibition in percent relative to the control is calculated. The antiproliferative activity is estimated using regression analysis.

EXAMPLE I

Tablet containing 50 mg of active compound

Composition:

| | |
|---|---|
| (1) Active compound | 50.0 mg |
| (2) Lactose | 98.0 mg |
| (3) Maize starch | 50.0 mg |
| (4) Polyvinylpyrrolidone | 15.0 mg |
| (5) Magnesium stearate | 2.0 mg |
| Total: | 215.0 mg |

Preparation:

(1), (2) and (3) are mixed and granulated with an aqueous solution of (4). The dried granules are admixed with (5). This mixture is tabletted.

EXAMPLE II
Capsule containing 50 mg of active compound
Composition:

| | |
|---|---|
| (1) Active compound | 50.0 mg |
| (2) Maize starch, dried | 58.0 mg |
| (3) Lactose powder | 50.0 mg |
| (4) Magnesium stearate | 2.0 mg |
| Total: | 160.0 mg |

Preparation:
(1) is ground with (3). This ground material is added with vigorous mixing to the mixture of (2) and (4). This powder mixture is, on a capsule filling machine, filled into hard gelatine capsules size 3.

TABLE 8

New Chinolyl-Derivatives with antitumoral activity

| Ex. | R | $R_1$ | $R_2$ | $R_3$ | X | Z | n | m | p | Q | $R_4$ | Code-Nr. | M/e (M + H) |
|---|---|---|---|---|---|---|---|---|---|---|---|---|---|
| 1 | H | H | H | H | N | O | 2 | 0 | $H_2$ | $H_2$ | | 24203 | 378 |
| 2 $H_{Cl}$-Salz | H | H | H | H | N | O | 2 | 0 | $H_2$ | $H_2$ | | 24203 | 378 |
| 3 | 2-(4-chloro=phenyl) | H | 6-$CH_3$ | 7-Cl | N | O | 2 | 0 | $H_2$ | $H_2$ | | 68780 | 537 |
| 4 | 2-$CH_3$ | 3-OH | H | H | N | O | 2 | 0 | $H_2$ | $H_2$ | | 68675 | 408 |
| 5 | 2-(3,4-dimeth=oxyphenyl) | H | H | 7-$CH_3$ | N | O | 2 | 0 | $H_2$ | $H_2$ | | 68823 | 528 |

We claim:
1. Quinoline derivatives according to the formula 1

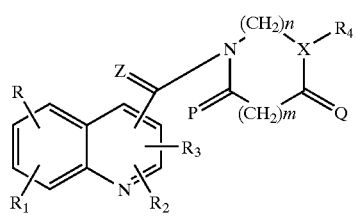

(1)

in which

R, $R_1$, $R_2$, $R_3$ can be attached to any of the quinoline carbon atoms $C_2$ to $C_8$, are identical or different and independently of one another denote hydrogen, straight-chain or branched $C_{1-8}$ alkyl, $C_{3-7}$ cycloalkyl, straight-chain or branched $C_{1-8}$ alkylcarbonyl, straight-chain or branched $C_{1-8}$ alkoxy, halogen, aryl-$C_{1-8}$ alkoxy, nitro, amino, mono-$C_{1-4}$ alkylamino, di-$C_{1-4}$ alkylamino, $C_{1-8}$ alkoxycarbonylamino, $C_{1-6}$ alkoxycarbonylamino-$C_{1-8}$ alkyl, cyano, straight-chain or branched cyano-$(C_1–C_6)$-alkyl, carboxyl, $C_{1-8}$ alkoxycarbonyl, $C_{1-4}$ alkyl which is substituted by one or more fluorine atoms, carboxy-$C_{1-8}$ alkyl or $C_{1-8}$ alkoxycarbonyl-$C_{1-6}$ alkyl, $C_{2-6}$ alkenyl, $C_{2-6}$ alkynyl, straight-chain or branched cyano-$C_{1-6}$ alkyl, aryl, where the aryl radical can be unsubstituted or mono- or polysubstituted by identical or different substituents from the group consisting of halogen, straight-chain or branched $C_{1-8}$ alkyl, $C_{3-7}$ cycloalkyl, carboxyl, straight-chain or branched $C_{1-8}$ alkoxycarbonyl, by trifluoromethyl, hydroxyl, straight-chain or branched $C_{1-8}$ alkoxy, benzyloxy, nitro, amino, mono-$C_{1-4}$ alkylamino, di-$C_{1-4}$ alkylamino, cyano, straight-chain or branched cyano-$C_{1-6}$ alkyl, where R and $R_1$ or $R_2$ and $R_3$ can form a fused aromatic 6-membered ring with the quinoline ring forming an acridine ring which for its part can be substituted at any C atom ring position by the radicals R, $R_1$, $R_2$ and $R_3$ having the meanings mentioned above;

P and Q are each 2 hydrogen atoms;

Z is oxygen or sulfur, where the radical

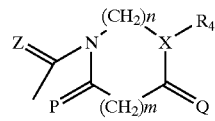

substituted on the quinoline heterocycle can be attached to C atoms $C_{2-8}$ of the quinoline ring skeleton;

X is nitrogen;

n is 1 or 2 and m is 0 or 1, with the proviso that the sum of n and m is 2;

$R_4$ is a straight-chain or branched $C_{2-20}$ alkenyl or alkynyl which can be unsaturated or can optionally be substituted at the same or different C atoms by one, two or more aryl, heteroaryl, halogen, cyano, $C_{1-6}$ alkoxycarbonylamino, $C_{1-6}$ alkoxy, amino, mono-$C_{1-4}$ alkylamino or di-$C_{1-4}$ alkylamino; a straight-chain or branched $C_{1-20}$ alkyl which can be unsubstituted or can optionally be substituted at the same or different C atoms by two or more aryl, heteroaryl, halogen, cyano, $C_{1-6}$ alkoxycarbonylamino, $C_{1-6}$ alkoxy, amino, mono-$C_{1-4}$ alkylamino or di-$C_{1-4}$ alkylamino; a straight-chain or branched $C_{1-20}$ alkyl which can be unsubstituted or can optionally be substituted at the same or different C atoms by one heteroaryl, halogen, cyano, $C_{1-6}$ alkoxycarbonylamino, $C_{1-6}$ alkoxy, amino, mono-$C_{1-4}$ alkylamino or di-$C_{1-4}$ alkylamino; a $C_{6-14}$ aryl radical, or a $C_{2-10}$ heteroaryl or $C_{2-10}$ heteroaryl-$C_{1-4}$ alkyl radical which contains one or more heteroatoms selected from the group consisting of N, O and S, where the $C_{1-4}$ alkyl radical can be unsubstituted or mono- or polysubstituted by identical or different substituents from the group consisting of $C_{1-6}$ alkyl, halogen or oxo (=O) and where the $C_{6-14}$ aryl or $C_{2-10}$ heteroaryl radical can be unsubstituted or mono- or polysubstituted by identical or different substituents from the group consisting of straight-chain or branched $C_{1-8}$ alkyl, $C_{3-7}$ cycloalkyl, halogen, cyano, $C_{1-6}$ alkoxycarbonylamino, $C_{1-6}$ alkoxy, carboxyl, $C_{1-8}$ alkoxycarbonyl, or straight-chain or branched $C_{1-6}$ alkyl which is substituted by one or more fluorine atoms, hydroxyl, straight-chain or branched $C_{1-8}$ alkoxy, where adjacent oxygen atoms can also be linked by $C_{1-2}$ alkylene groups, benzyloxy, nitro, amino, mono-$C_{1-4}$ alkylamino, di-$C_{1-4}$ alkylamino, or aryl, which can be unsubstituted or mono- or polysubstituted by identical or different substituents from the group consisting of straight-chain or branched $C_{1-8}$ alkyl, $C_{3-7}$ cycloalkyl, carboxyl, straight-chain or branched $C_{1-8}$ alkoxycarbonyl, trifluoromethyl, hydroxyl, straight-chain or branched $C_{1-8}$ alkoxy, benzyloxy, nitro, amino, mono-$C_{1-4}$ alkylamino, di-$C_{1-4}$ alkylamino, cyano, straight-chain or branched cyano-$C_{1-6}$ alkyl; or $C_{6-14}$ aryl-$C_{1-4}$ alkyl radical, where the $C_{1-4}$ alkyl radical can be unsubstituted or mono- or polysubstituted by identical or different substituents from the group consisting of $C_{1-6}$ alkyl, halogen or oxo (=O) and where the $C_{6-14}$ aryl is mono- or polysubstituted by identical or different substituents from the group consisting of straight-chain or branched $C_{1-8}$ alkyl, $C_{3-7}$ cycloalkyl, halogen, cyano, $C_{1-6}$ alkoxycarbonylamino, carboxyl, $C_{1-8}$ alkoxycarbonyl, or straight-chain or branched $C_{1-6}$ alkyl which is substituted by one or more fluorine atoms, hydroxyl, straight-chain or branched $C_{1-8}$ alkoxy, where adjacent oxygen atoms can also be linked by $C_{1-2}$ alkylene groups, benzyloxy, nitro, amino, mono-$C_{1-4}$ alkylamino, di-$C_{1-4}$ alkylamino, or aryl, which can be unsubstituted or mono- or polysubstituted by identical or different substituents from the group consisting of straight-chain or branched $C_{1-8}$ alkyl, $C_{3-7}$ cycloalkyl, carboxyl, straight-chain or branched $C_{1-8}$ alkoxycarbonyl, trifluoromethyl, hydroxyl, straight-chain or branched $C_{1-8}$ alkoxy, benzyloxy, nitro, amino, mono-$C_{1-4}$ alkylamino, di-$C_{1-4}$ alkylamino, cyano, straight-chain or branched cyano-$C_{1-6}$ alkyl;

and their structural isomers and stereoisomers and their pharmaceutically acceptable salts.

2. A pharmaceutical composition which comprises as active ingredient at least one quinoline derivative according of claim 1, together with pharmaceutically acceptable carrier.

3. The pharmaceutically acceptable acid addition salt of the quinoline derivative of claim 1, when formed with one of the acids hydrochloric acid, hydrobromic acid, sulfuric acid, phosphoric acid, fumaric acid, succinic acid, lactic acid, citric acid, acetic acid, tartaric acid, malic acid, maleic acid, embonic acid, malonic acid, trifluoroacetic acid, methanesulfonic acid, and sulfoacetic acid.

4. The quinoline derivative of claim 1, wherein in R, $R_1$, $R_2$ and $R_3$, said $C_{1-8}$ alkylcarbonyl is acetyl, said $C_{1-8}$ alkoxy is benzyloxy or phenylethoxy, said $C_{1-4}$ alkyl which is substituted by one or more fluorine atoms is trifluoromethyl, said $C_{2-6}$ alkenyl is allyl, said $C_{2-6}$ alkynyl is ethynyl or propargyl, said cyano-$C_{1-6}$ alkyl is cyanomethyl, said $C_{1-8}$ alkoxy-carbonyl is tert-butoxycarbonyl, and said $C_{1-8}$ alkoxy is methoxy or ethoxy, and in $R_4$ said $C_{1-6}$ alkyl which is substituted by one or more fluorine atoms is trifluoromethyl, said $C_{1-8}$ alkoxy is methoxy or ethoxy, and said $C_{1-2}$ alkylene group is a methylene group.

5. The quinoline derivative of formula 1 of claim 1, wherein R, $R_1$, $R_2$, $R_3$, X, Z, P, Q, n and m have the meanings given in claim 1;

$R_4$ is a straight-chain or branched $C_{2-20}$ alkenyl or alkynyl radical which can be unsubstituted or optionally substituted on the same or different C atoms by one, two or more aryl, heteroaryl, halogen, $C_{1-6}$ alkoxy, amino, mono- $C_{1-4}$ alkylamino or di-$C_{1-4}$ alkylamino; a straight-chain or branched $C_{1-20}$ alkyl radical which can be unsubstituted or optionally substituted on the same or different C atoms by two or more aryl, heteroaryl, halogen, $C_{1-6}$ alkoxy, amino, mono-$C_{1-4}$ alkylamino or di-$C_{1-4}$ alkylamino; or a straight-chain or branched $C_{1-20}$ alkyl radical which can be unsubstituted or optionally substituted on the same or different C atoms by one heteroaryl, halogen, $C_{1-6}$ alkoxy, amino, mono-$C_{1-4}$ alkylamino or di-$C_{1-4}$ alkylamino;

a phenyl ring or a naphthyl ring, each of which can be unsubstituted or mono- or polysubstituted by the same or different substituents from the group of straight-chain or branched $C_{1-8}$ alkyl, $C_{3-7}$ cycloalkyl, halogen, cyano, $C_{1-6}$ alkoxycarbonylamino, $C_{1-6}$ alkoxy, carboxyl, $C_{1-6}$ alkoxycarbonyl, straight-chain or branched $C_{1-6}$ alkyl which is substituted by one or more fluorine atoms, hydroxyl, straight-chain or branched $C_{1-6}$ alkoxy, benzyloxy, nitro, amino, mono-$C_{1-4}$ alkylamino, di-$C_{1-4}$ alkylamino, aryl, which can be unsubstituted or mono- or polysubstituted by the same or different substituents from the group of straight-chain or branched $C_{1-8}$ alkyl, $C_{3-7}$ cycloalkyl, carboxyl, straight-chain or branched $C_{1-8}$ alkoxycarbonyl, by trifluoromethyl, hydroxyl, straight-chain or branched $C_{1-8}$ alkoxy, benzyloxy, nitro, amino, mono-$C_{1-4}$ alkylamino, di-$C_{1-4}$ alkylamino, cyano, straight-chain or branched cyano-$C_{1-6}$ alkyl;

a 2-, 4-, 5- or 6-pyrimidinyl radical, or a 2-, 4-, 5- or 6-pyrimidinyl-$C_{1-4}$ alkyl radical, wherein the $C_{1-4}$ alkyl radical can be unsubstituted or mono- or polysubstituted by the same or different substituents from the group of $C_{1-6}$ alkyl, halogen or oxo (=O) and the 2-, 4-, 5- or 6-pyrimidinyl radical can be unsubstituted or mono- or up to trisubstituted by the same or different substituents from the group of hydrogen, or Y wherein Y is a $C_{1-6}$ alkyl, halogen, nitro, amino, mono-$C_{1-6}$ alkylamino, di-$C_{1-6}$ alkylamino, hydroxyl, $C_{1-6}$ alkoxy, benzyloxy, carboxyl, $C_{1-6}$ alkoxycarbonyl, $C_{1-6}$ alkoxycarbonylamino or $C_{1-6}$ alkyl which is mono- or polysubstituted by fluorine, $C_{6-10}$ aryl and $C_{6-10}$ aryl-$C_{1-6}$ alkyl;

a 3-, 4-, 5- or 6-pyridazinyl radical, or a 3-, 4-, 5- or 6pyridazinyl-$C_{1-4}$ alkyl radical, wherein the $C_{1-4}$ alkyl radical can be unsubstituted or mono- or polysubstituted by the same or different substituents from the group of $C_{1-6}$ alkyl, halogen or oxo (=O), and the 3-, 4-, 5- or 6-pyridazinyl radical can be unsubstituted or mono- or up to trisubstituted by the same or different substituents from the group of hydrogen, or Y;

a 2-, 3-, 5- or 6-pyrazinyl radical, or a 2-, 3-, 5- or 6-pyrazinyl-$C_{1-4}$ alkyl radical, wherein the $C_{1-4}$ alkyl radical can be unsubstituted or mono- or polysubstituted by the same or different substituents from the group of $C_{1-6}$ alkyl, halogen or oxo (=O), and the 2-, 3-, 5- or 6-pyrazinyl radical can be unsubstituted or mono- or up to trisubstituted by the same or different substituents from the group of hydrogen, or Y;

a 3-, 4-, 5-, 6-, 7-, or 8-cinnolinyl radical, or a 3-, 4-, 5-, 6-, 7-, or 8-cinnolinyl-$C_{1-4}$ alkyl radical, wherein the $C_{1-4}$ alkyl radical can be unsubstituted or mono- or polysubstituted by the same or different substituents from the group of $C_{1-4}$ alkyl, halogen or oxo (=O), and the 3-, 4-, 5-, 6-, 7-, or 8-cinnolinyl radical can be unsubstituted or mono- or up to pentasubstituted by the same or different substituents from the group of hydrogen, or Y;

a 2-, 4-, 5-, 6-, 7-, or 8-quinazolinyl radical, or a 2-, 4-, 5-, 6-, 7 or 8-quinazolinyl-$C_{1-4}$ alkyl radical, wherein the $C_{1-4}$ alkyl radical can be unsubstituted or mono- or polysubstituted by the same or different substituents from the group or hydrogen, $C_{1-6}$ alkyl, halogen or oxo (=O), and the 2-, 4-, 5-, 6-, 7-, or 8-quinazolinyl radical can be unsubstituted or mono- or up to pentasubstituted by the same or different substituents from the group of hydrogen, or Y;

a 2-, 3-, 5-, 6-, 7-, or 8-quinoxalinyl radical, or a 2-, 3-, 5-, 6-, 7-, or 8-quinoxalinyl-$C_{1-4}$ alkyl radical, wherein the $C_{1-4}$ alkyl radical can be unsubstituted or mono- or polysubstituted by the same or different substituents from the group of $C_{1-6}$ alkyl, halogen or oxo (=O), and the 2-, 3-, 5-, 6-, 7-, or 8-quinoxalinyl radical can be unsubstituted or mono- or up to pentasubstituted by the same or different substituents from the group of hydrogen, or Y;

a 1-, 4-, 5-, 6-, 7-, or 8-phthalazinyl radical, or a 1-, 4-, 5-, 6-, 7-, or 8-phthalazinyl-$C_{1-4}$ alkyl radical, wherein the $C_{1-4}$ alkyl radical can be unsubstituted or mono- or polysubstituted by the same or different substituents from the group of $C_{1-6}$ alkyl, halogen or oxo (=O), and the 1-, 4-, 5-, 6-, 7-, or 8-phthalazinyl radical can be unsubstituted or mono- or up to pentasubstituted by the same or different substituents from the group of hydrogen, or Y;

a 2-, 3-, 4-, 5-, 6-, 7- or 8-quinolyl radical, or a 2-, 3-, 4-, 5-, 6-, 7 or 8-quinolyl-$C_{1-4}$ alkyl radical, wherein the $C_{1-4}$ alkyl radical can be unsubstituted or mono- or polysubstituted by the same or different substituents from the group of $C_{1-6}$ alkyl, halogen or oxo (=O), and the 2-, 3-, 4-, 5-, 6-, 7- or 8-quinolyl radical can be unsubstituted or mono- or up to hexasubstituted by the same or different substituents from the group of hydrogen, or Y;

a 1-, 3-, 4-, 5-, 6-, 7- or 8-isoquinolyl radical, or a 1-, 3-, 4-, 5-, 6-, 7- or 8-isoquinolyl-$C_{1-4}$ alkyl radical, wherein the $C_{1-4}$ alkyl radical can be unsubstituted or mono- or polysubstituted by the same or different substituents from the group of $C_{1-6}$ alkyl, halogen or oxo (=O), and the 1-, 4-, 5-, 6-, 7- or 8-isoquinolyl radical can be unsubstituted or mono- or up to hexasubstituted by the same or different substituents from the group of hydrogen, or Y;

a 2-, 6-, 8- or 9-[9H]-purinyl radical, or a 2-, 6-, 8- or 9-[9H]-purinyl-$C_{1-4}$ alkyl radical, wherein the $C_{1-4}$ alkyl radical can be unsubstituted or mono- or polysubstituted by the same or different substituents from the group of $C_{1-6}$ alkyl, halogen or oxo (=O), and the 2-, 6-, 8- or 9-[9H]-purinyl radical can be unsubstituted or mono- to trisubstituted by the same or different substituents from the group of hydrogen, or Y;

a 2-, 6-, 7- or 8-[7H]-purinyl radical, or a 2-, 6-, 7- or 8-[7H]-purinyl-$C_{1-4}$ alkyl radical, wherein the $C_{1-4}$ alkyl radical can be unsubstituted or mono- or polysubstituted by the same or different substituents from the group of $C_{1-6}$ alkyl, halogen or oxo (=O), and the 2-, 6-, 7- or 8-[7H]-purinyl radical can be unsubstituted or mono- or up to trisubstituted by the same or different substituents from the group of hydrogen, or Y;

a 1-, 2-, 3-, 4-, 5-, 6-, 7-, 8- or 9-acridinyl radical, or a 1-, 2-, 3-, 4-, 5-, 6-, 7-, 8- or 9-acridinyl-$C_{1-4}$ alkyl radical, where the $C_{1-6}$ alkyl radical can be unsubstituted or mono- or polysubstituted by the same or different substituents from the group of $C_{1-6}$ alkyl, halogen or oxo (=O), and the 1-, 2-, 3-, 4-, 5-, 6-, 7-, 8- or 9-acridinyl radical can be unsubstituted or mono- to octasubstituted by the same or different substituents from the group of hydrogen, or Y;

a 1-, 2-, 3-, 4-, 5-, 6-, 7-, 8- or 9-phenanthridinyl radical, or a 1-, 2-, 3-, 4-, 5-, 6-, 7-, 8- or 9- phenanthridinyl-$C_{1-6}$ alkyl radical, wherein the $C_{1-6}$ alkyl radical can be unsubstituted or mono- or polysubstituted by the same or different substituents from the group of hydrogen, $C_{1-6}$ alkyl, halogen or oxo (=O), and the 1-, 2-, 3-, 4-, 5-, 6-, 7-, 8- or 9-phenanthridinyl radical can be unsubstituted or mono- or up to octasubstituted by the same or different substituents of Y;

a 2-, 3-, 4-, 5- or 6-pyridyl radical where the 2-, 3-, 4-, 5- or 6pyridyl radical an be unsubstituted or mono- or up to tetrasubstituted by the same or different substituents from the group of hydrogen, or Y;

a 2-, 3-, 4-, 5- or 6-pyridinyl-$C_{1-6}$ alkyl radical, wherein the $C_{1-6}$ alkyl radical can be unsubstituted or mono- or polysubstituted by the same or different substituents from the group of $C_{1-6}$ alkyl, halogen or oxo (=O), and the 2-, 3-, 4-, 5- or 6-pyridinyl radical can be unsubstituted or mono- or up to tetrasubstituted by the same or different substituents from the group of hydrogen, or Y;

a 2-, 3-, 4- or 5-thienyl radical, or a 2-, 3-, 4- or 5-thienyl-$C_{1-6}$ alkyl radical wherein the $C_{1-6}$ alkyl radical can be unsubstituted or mono- or polysubstituted by the same or different substituents from the group of $C_{1-6}$ alkyl, halogen or oxo (=O), and the 2-, 3-, 4- or 5-thienyl radical can be unsubstituted or mono- or up to trisubstituted by the same or different substituents from the group of hydrogen, or Y;

a 2-, 4-, or 5-thiazolyl radical, or a 2-, 4-, or 5-thiazolyl $C_{1-6}$ alkyl $C_{1-6}$ alkyl radical, wherein the $C_{1-6}$ alkyl radical can be unsubstituted or mono- or polysubstituted by the same or different substituents from the group of $C_{1-6}$ alkyl, halogen or oxo (=O), and the 2-, 4-, or 5-thiazolyl radical can be unsubstituted or mono- or disubstituted by the same or different substituents from the group of hydrogen, or Y;

a 3-, 4-, or 5-isothiazolyl radical, or a 3-, 4-, or 5-isothiazolyl-$C_{1-6}$ alkyl radical, wherein the $C_{1-6}$ alkyl radical can be unsubstituted or mono- or polysubstituted by the same or different substituents from the group of $C_{1-6}$ alkyl, halogen or oxo (=O), and the 3-, 4-, or 5-isothiazolyl radical can be unsubstituted or mono- or disubstituted by the same or different substituents from the group of hydrogen, or Y;

a 2-, 4-, 5-, 6-, or 7-benzothiazolyl radical, or a 2-, 4-, 5-, 6-, or 7-benzothiazolyl-$C_{1-6}$ alkyl radical, wherein the $C_{1-6}$ alkyl radical can be unsubstituted or mono- or polysubstituted by the same or different substituents from the group of $C_{1-6}$ alkyl, halogen or oxo (=O),and the 2-, 4-, 5-, 6-, or 7-benzothiazolyl radical can be unsubstituted or mono- or up to tetrasubstituted by the same or different substituents from the group of hydrogen, or Y;

a 1-, 2-, 4-, or 5-imidazolyl radical, or a 1-, 2-, 4-, or 5 imidazolyl-$C_{1-6}$ alkyl radical, wherein the $C_{1-6}$ alkyl radical can be unsubstituted or mono- or polysubstituted by the same or different substituents from the group of $C_{1-6}$ alkyl, halogen or oxo (=O), and the 1-, 2-, 4-, or 5-imidazolyl radical can be unsubstituted or mono- or up to trisubstituted by the same or different substituents from the group of hydrogen, or Y;

a 1-, 3-, 4-, or 5-pyrazolyl radical, or a 1-, 3-, 4- or 5-pyrazolyl-$C_{1-6}$ alkyl radical, wherein the $C_{1-6}$ alkyl radical can be unsubstituted or mono- or polysubstituted by the same or different substituents from the group of $C_{1-6}$ alkyl, halogen or oxo (=O), and the 1-, 3- , 4- or 5-pyrazolyl radical can be unsubstituted or mono- or up to trisubstituted by the same of different substituents from the group of hydrogen, or Y;

a 1-, 2-, 3-, 4-, or 5-pyrrolyl radical, or a 1-, 2-, 3-, 4-, or 5-pyrrolyl-$C_{1-6}$ alkyl radical, wherein the $C_{1-6}$ alkyl radical can be unsubstituted or mono- or polysubstituted by the same or different substituents from the group of $C_{1-6}$ alkyl, halogen or oxo (=O), and the 1-, 2-, 3-, 4- or 5-pyrrolyl radical can be unsubstituted or mono- or up to tetrasubstituted by the same or different substituents from the group of hydrogen, or Y;

a 1-, 3-, or 5-[1.2.4]-triazolyl radical, or a 1-, 3-, or 5-[1.2.4]-triazolyl-$C_{1-6}$ alkyl radical, wherein the $C_{1-6}$ alkyl radical can be unsubstituted or mono- or polysubstituted by the same or different substituents from the group of hydrogen, $C_{1-6}$ alkyl, halogen or oxo (=O), and the 1-, 3-, or 5-[1.2.4]-triazolyl radical can be unsubstituted or mono- or disubstituted by the same or different substituents from Y;

a 1-, 4-, or 5-[1.2.3]-triazolyl radical, or a 1-, 4-, or 5-[1.2.3]-triazolyl-$C_{1-6}$ alkyl radical, wherein the $C_{1-6}$ alkyl radical can be unsubstituted or mono- or polysubstituted by the same or different substituents from the group of $C_{1-6}$ alkyl, halogen or oxo (=O), and the 1-, 4-, or 5-[1.2.3]-triazolyl radical can be unsubstituted or mono- or disubstituted by the same or different substituents from the group of hydrogen, or Y;

a 1- or 5-[1H]-tetrazolyl radical, or a 1-, or 5-[1H]-tetrazolyl-$C_{1-6}$ alkyl radical, wherein the $C_{1-6}$ alkyl radical can be unsubstituted or mono- or polysubstituted by the same or different substituents from the group of $C_{1-6}$ alkyl, halogen or oxo (=O), and the 1-, or 5-[1H]-tetrazolyl radical can be unsubstituted or substituted by hydrogen, or Y;

a 2- or 5-[2H]-tetrazoyl radical, or a 2- or 5-[2H]-tetrazolyl-$C_{1-6}$ alkyl radical, wherein the $C_{1-6}$ alkyl radical can be unsubstituted or mono- or polysubstituted by the same or different substituents from the group of $C_{1-6}$ alkyl, halogen or oxo (=O), and the 2- or 5-[2H]-tetrazolyl radical can be unsubstituted or substituted by hydrogen, or Y;

a 2-, 4-, or 6-[1.3.5]-triazinyl radical, or a 2-, 4-, or 6-[1.3.5]-triazinyl-$C_{1-6}$ alkyl radical, wherein the $C_{1-6}$ alkyl radical can be unsubstituted or mono- or polysubstituted by the same or different substituents from the group of hydrogen, $C_{1-6}$ alkyl, halogen or oxo (=O), and the 2-, 4-, or 6-[1.3.5]-triazinyl radical can be unsubstituted or mono- or disubstituted by the same or different substituents from the group of hydrogen, or Y;

a 2-, 4-, or 5-oxazolyl radical, or a 2-, 4-, or 5-oxazolyl-$C_{1-6}$ alkyl radical, wherein the $C_{1-6}$ alkyl radical can be unsubstituted or mono- or polysubstituted by the same or different substituents from the group of $C_{1-6}$ alkyl, halogen or oxo (=O), and the 2-, 4-, or 5-oxazolyl radical can be unsubstituted or mono- or disubstituted by the same or different substituents from the group of hydrogen, or Y;

a 3-, 4-, or 5-isoxazolyl radical, or a 3-, 4-, or 5-isoxazolyl-$C_{1-6}$ alkyl radical, wherein the $C_{1-6}$ alkyl radical can be unsubstituted or mono- or polysubstituted by the same or different substituents from the group of $C_{1-6}$ alkyl, halogen or oxo (=O), and the 3-, 4- , or 5-isoxazolyl radical can be unsubstituted or mono- or disubstituted by the same or different substituents from the group of hydrogen, or Y;

a 1-, 2-, 3-, 4-, 5-, 6- or 7-indolyl radical, or a 1-, 2-, 3-, 4-, 5-, 6 or 7-indolyl $C_{1-6}$ alkyl radical, wherein the $C_{1-6}$ alkyl radical can be unsubstituted or mono- or polysubstituted by the same or different substituents from the group of $C_{1-6}$ alkyl, halogen or oxo (=O), and the 1-, 2-, 3-, 4-, 5-, 6- or 7-indolyl radical can be unsubstituted or mono- or up to hexasubstituted by the same or different substituents from the group of hydrogen, or Y.

6. The quinoline derivative of claim 1, wherein in $R_4$ said $C_{1-6}$ alkyl which is substituted by one or more fluorine atoms is trifluoromethyl, and said $C_{1-8}$ alkoxy is methoxy or ethoxy.

7. The quinoline derivative of claim 1, wherein R, $R_1$, $R_2$, $R_3$, X, Z, P, Q, n and m have the meanings given above, and $R_4$ is phenyl which is unsubstituted or substituted by one to five the same or different $C_{1-6}$ alkoxy groups, where adjacent oxygen atoms can also be linked by $C_{1-2}$ alkylene groups.

8. The quinoline derivative of claim 1, wherein R, $R_1$, $R_2$, $R_3$, X, Z, P, Q, n and m have the meanings given above and $R_4$ is 3,5-dimethoxyphenyl.

9. The quinoline derivative of claim 1, wherein $R_4$ has the meanings given above, R, $R_1$, $R_2$, $R_3$ each is hydrogen, Z is an oxygen atom, X is a nitrogen atom, P and Q are each two hydrogen atoms as in —$CH_2$—, m is zero, and n is 2.

10. The quinoline derivative of claim 1, wherein R, $R_1$, $R_2$, $R_3$ are each a hydrogen atom, Z is an oxygen atom, X is a nitrogen atom, P and Q each are two hydrogen atoms as in —$CH_2$—, m is zero, n is 2, and $R_4$ is a 3,5-dimethoxyphenyl radical.

11. A method for treating a cancer in a mammal, which comprises administering to a mammal in need thereof an effective amount of a quinoline derivative according to the formula 1

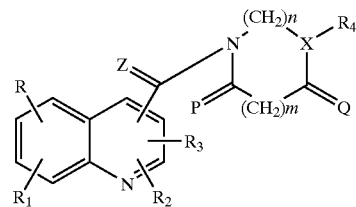

in which

R, $R_1$, $R_2$, $R_3$ can be attached to any of the quinoline carbon atoms $C_2$ to $C_8$, are identical or different and independently of one another denote hydrogen, straight-chain or branched $C_{1-8}$ alkyl, $C_{3-7}$ cycloalkyl, straight-chain or branched $C_{1-8}$ alkylcarbonyl, straight-chain or branched $C_{1-8}$ alkoxy, halogen, aryl-$C_{1-8}$ alkoxy, nitro, amino, mono-$C_{1-4}$ alkylamino, di-$C_{1-4}$ alkylamino, $C_{1-8}$ alkoxycarbonylamino, $C_{1-6}$ alkoxycarbonylamino-$C_{1-8}$ alkyl cyano, straight-chain or branched cyano-$(C_1-C_6)$-alkyl, carboxyl, $C_{1-8}$ alkoxycarbonyl, $C_{1-4}$ alkyl which is substituted by one or more fluorine atoms, carboxy-$C_{1-8}$ alkyl or $C_{1-8}$ alkoxycarbonyl-$C_{1-6}$ alkyl, $C_{2-6}$ alkenyl, $C_{2-6}$ alkynyl, straight-chain or branched cyano-$C_{1-6}$ alkyl, aryl, where the aryl radical can be unsubstituted or mono- or polysubstituted by identical or different substituents from the group consisting of halogen, straight-chain or branched $C_{1-8}$ alkyl, $C_{3-7}$ cycloalkyl, carboxyl, straight-chain or branched $C_{1-8}$ alkoxycarbonyl, by trifluoromethyl, hydroxyl, straight-chain or branched $C_{1-8}$ alkoxy, benzyloxy, nitro, amino, mono-$C_{1-4}$ alkylamino, di-$C_{1-4}$ alkylamino, cyano, straight-chain or branched cyano-$C_{1-6}$ alkyl, where R and $R_1$ or $R_2$ and $R_3$ can form a fused aromatic 6-membered ring with the quinoline ring forming an acridine ring which for its part can be substituted at any C atom ring position by the radicals R, $R_1$, $R_2$ and $R_3$ having the meanings mentioned above;

P and Q are each 2 hydrogen atoms;

Z is oxygen or sulfur, where the radical

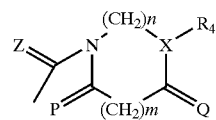

substituted on the quinoline heterocycle can be attached to C atoms $C_{2-8}$ of the quinoline ring skeleton;

X is nitrogen;

n is 1 or 2 and m is 0 or 1, with the proviso that the sum of n and m is 2;

$R_4$ is a straight-chain or branched $C_{1-20}$ alkyl, $C_{2-20}$ alkenyl or $C_{2-20}$ alkynyl radical which can be unsubstituted or can optionally be substituted at the same or different C atoms by one, two or more aryl, heteroaryl, halogen, cyano, $C_{1-6}$ alkoxycarbonylamino, $C_{1-6}$ alkoxy, amino, mono-$C_{1-4}$ alkylamino or di-$C_{1-4}$ alkylamino; a $C_{6-14}$ aryl radical, $C_{6-14}$ aryl-$C_{1-4}$ alkyl radical, or a $C_{2-10}$ heteroaryl or $C_{2-10}$ heteroaryl-$C_{1-4}$ alkyl radical which contains one or more heteroatoms selected from the group consisting of N, O and S, where the $C_{1-4}$ alkyl radical can be unsubstituted or mono- or polysubstituted by identical or different substituents from the group consisting of $C_{1-6}$ alkyl, halogen or oxo (=O) and where the $C_{6-14}$ aryl or $C_{2-10}$ heteroaryl radical can be unsubstituted or mono- or polysubstituted by identical or different substituents from the group consisting of straight-chain or branched $C_{1-8}$ alkyl, $C_{3-7}$ cycloalkyl, halogen, cyano, $C_{1-6}$ alkoxycarbonylamino, $C_{1-6}$ alkoxy, carboxyl, $C_{1-8}$ alkoxycarbonyl, or straight-chain or branched $C_{1-6}$ alkyl which is substituted by one or more fluorine atoms, hydroxyl, straight-chain or branched $C_{1-8}$ alkoxy, where adjacent oxygen atoms can also be linked by $C_{1-2}$ alkylene groups, benzyloxy, nitro, amino, mono-$C_{1-4}$ alkylamino, di-$C_{1-4}$ alkylamino, or aryl, which can be unsubstituted or mono- or polysubstituted by identical or different substituents from the group consisting of straight-chain or branched $C_{1-8}$ alkyl, $C_{3-7}$ cycloalkyl, carboxyl, straight-chain or branched $C_{1-8}$ alkoxycarbonyl, trifluoromethyl, hydroxyl, straight-chain or branched $C_{1-8}$ alkoxy, benzyloxy, nitro, amino, mono-$C_{1-4}$ alkylamino, di-$C_{1-4}$ alkylamino, cyano, straight-chain or branched cyano-$C_{1-6}$ alkyl;

and their structural isomers and stereoisomers and their pharmaceutically acceptable salts;

wherein said cancer is selected from the group consisting of cervical carcinoma, lymphocyte leukemia, breast adenocarcinoma, ovarian adenocarcinoma, and pulmonary carcinoma.

12. The method of claim 11, wherein $R_4$ is a straight-chain or branched $C_{2-20}$ alkenyl or alkynyl which can be unsubstituted or can optionally be substituted at the same or different C atoms by one, two or more aryl, heteroaryl, halogen, cyano, $C_{1-6}$ alkoxycarbonylamino, $C_{1-6}$ alkoxy, amino, mono-$C_{1-4}$ alkylamino or di-$C_{1-4}$ alkylamino; a straight-chain or branched $C_{1-20}$ alkyl which can be unsubstituted or can optionally be substituted at the same or different C atoms by two or more aryl heteroaryl, halogen, cyano, $C_{1-6}$ alkoxycarbonylamino, $C_{1-6}$ alkoxy, amino, mono-$C_{1-4}$ alkylamino or di-$C_{1-4}$ alkylamino; a straight-chain or branched $C_{1-20}$ alkyl which can be unsubstituted or can optionally be substituted at the same or different C atoms by one heteroaryl, halogen, cyano, $C_{1-6}$ alkoxycarbonylamino, $C_{1-6}$ alkoxy, amino, mono-$C_{1-4}$ alkylamino or di-$C_{1-4}$ alkylamino; a straight-chain or branched $C_{1-20}$ alkyl which can be unsubstituted or can optionally be substituted at the same or different C atoms by one heteroaryl, halogen, cyano, $C_{1-6}$ alkoxycarbonylamino, $C_{1-6}$ alkoxy, amino, mono-$C_{1-4}$ alkylamino or di-$C_{1-4}$ alkylamino; a $C_{6-14}$ aryl radical, or a $C_{2-10}$ heteroaryl or $C_{2-10}$ heteroaryl-$C_{1-4}$ alkyl radical which contains one or more heteroatoms selected from the group consisting of N, O and S, where the $C_{1-4}$ alkyl radical can be unsubstituted or mono- or polysubstituted by identical or different substituents from the group consisting of $C_{1-6}$ alkyl, halogen or oxo (=O) and where the $C_{6-14}$ aryl or $C_{2-10}$ heteroaryl radical can be unsubstituted or mono- or polysubstituted by identical or different substituents from the group consisting of straight-chain or branched $C_{1-8}$ alkyl, $C_{3-7}$ cycloalkyl, halogen, cyano, $C_{1-6}$ alkoxycarbonylamino, $C_{1-6}$ alkoxy, carboxyl, $C_{1-8}$ alkoxycarbonyl, or straight-chain or branched $C_{1-6}$ alkyl which is substituted by one or more fluorine atoms, hydroxyl, straight-chain or branched $C_{1-8}$ alkoxy, where adjacent oxygen atoms can also be linked by $C_{1-2}$ alkylene groups, benzyloxy, nitro, amino, mono-$C_{1-4}$ alkylamino, di-$C_{1-4}$ alkylamino, or aryl, which can be unsubstituted or mono- or polysubstituted by identical or different substituents from the group consisting of straight-chain or branched $C_{1-8}$ alkyl, $C_{3-7}$ cycloalkyl, carboxyl, straight-chain or branched $C_{1-8}$ alkoxycarbonyl, trifluoromethyl, hydroxyl, straight-chain or branched $C_{1-8}$ alkoxy, benzyloxy, nitro, amino, mono-$C_{1-4}$ alkylamino, di-$C_{1-4}$ alkylamino, cyano, straight-chain or branched cyano-$C_{1-6}$ alkyl; or $C_{6-14}$ aryl-$C_{1-4}$ alkyl radical, where the $C_{1-4}$ alkyl radical can be unsubstituted or mono- or polysubstituted by identical or different substituents from the group consisting of $C_{1-6}$ alkyl, halogen or oxo (=O) and where the $C_{6-14}$ aryl is mono- or polysubstituted by identical or different substituents from the group consisting of straight-chain or branched $C_{1-8}$ alkyl, $C_{3-7}$ cycloalkyl, halogen, cyano, $C_{1-6}$ alkoxycarbonylamino, carboxyl, $C_{1-8}$ alkoxycarbonyl, or straight-chain or branched $C_{1-6}$ alkyl which is substituted by one or more fluorine atoms, hydroxyl, straight-chain or branched $C_{1-8}$ alkoxy, where adjacent oxygen atoms can also be linked by $C_{1-2}$ alkylene groups, benzyloxy, nitro, amino, mono-$C_{1-4}$ alkylamino, di-$C_{1-4}$ alkylamino, or aryl, which can be unsubstituted or mono- or polysubstituted by identical or different substituents from the group consisting of straight-chain or branched $C_{1-8}$ alkyl, $C_{3-7}$ cycloalkyl, carboxyl, straight-chain or branched $C_{1-8}$ alkoxycarbonyl, trifluoromethyl, hydroxyl, straight-chain or branched $C_{1-8}$ alkoxy, benzyloxy, nitro, amino, mono-$C_{1-4}$ alkylamino, di-$C_{1-4}$ alkylamino, cyano, straight-chain or branched cyano-$C_{1-6}$ alkyl.

13. A method for inhibiting the growth of tumor cells in mammal, comprising administering to a mammal in need thereof a tumor inhibiting amount of a quinoline derivative according to the formula 1

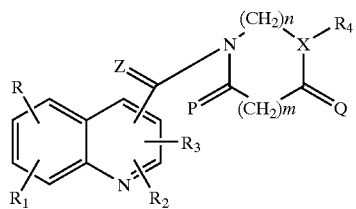

in which
R, $R_1$, $R_2$, $R_3$ can be attached to any of the quinoline carbon atoms $C_2$ to $C_8$, are identical or different and independently of one another denote hydrogen, straight-chain or branched $C_{1-8}$ alkyl, $C_{3-7}$ cycloalkyl, straight-chain or branched $C_{1-8}$ alkylcarbonyl, straight-chain or branched $C_{1-8}$ alkoxy, halogen, aryl-$C_{1-8}$ alkoxy, nitro, amino, mono-$C_{1-4}$ alkylamino, di-$C_{1-4}$ alkylamino, $C_{1-8}$ alkoxycarbonylamino, $C_{1-6}$ alkoxycarbonylamino-$C_{1-8}$ alkyl, cyano, straight-chain or branched cyano-$(C_1-C_6)$-alkyl, carboxyl, $C_{1-8}$ alkoxycarbonyl, $C_{1-4}$ alkyl which is substituted by one or more fluorine atoms, carboxy-$C_{1-8}$ alkyl or $C_{1-8}$ alkoxycarbonyl-$C_{1-6}$ alkyl, $C_{2-6}$ alkenyl, $C_{2-6}$ alkynyl, straight-chain or branched cyano-$C_{1-6}$ alkyl, aryl, where the aryl radical can be unsubstituted or mono- or polysubstituted by identical or different substituents from the group consisting of halogen, straight-chain or branch $C_{1-8}$ alkyl, $C_{3-7}$ cycloalkyl, carboxyl, straight-chain or branched $C_{1-8}$ alkoxycarbonyl, by trifluoromethyl, hydroxyl, straight-chain or branched $C_{1-8}$ alkoxy, benzyloxy, nitro, amino, mono-$C_{1-4}$ alkylamino, di-$C_{1-4}$ alkylamino, cyano, straight-chain or branched cyano-$C_{1-6}$ alkyl, where R and $R_1$ or $R_2$ and $R_3$ can form a fused aromatic 6-membered ring with the quinoline ring forming an acridine ring which or its part can be substituted at any C atom ring position by the radicals R, $R_1$, $R_2$ and $R_3$ having the meanings mentioned above;

P and Q are each 2 hydrogen atoms;
Z is oxygen or sulfur, where the radical

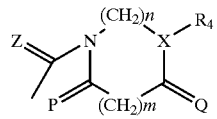

substituted on the quinoline heterocycle can be attached to C atoms $C_{2-8}$ of the quinoline ring skeleton;

X is nitrogen;
n is 1 or 2 and m is 0 or 1, with the proviso that the sum of n and m is 2;
$R_4$ is a straight-chain or branched $C_{1-20}$ alkyl, alkenyl or alkynyl radical which can be unsubstituted or can optionally be substituted at the same or different C atoms by one, two or more aryl, heteroaryl, halogen, cyano, $C_{1-6}$ alkoxycarbonylamino, $C_{1-6}$ alkoxy, amino, mono-$C_{1-4}$ alkylamino or di-$C_{1-4}$ alkylamino; a $C_{6-14}$ aryl radical, $C_{6-14}$ aryl-$C_{1-4}$ alkyl radical, or a $C_{2-10}$ heteroaryl or $C_{2-10}$ heteroaryl-$C_{1-4}$ alkyl radical which contains one or more heteroatoms selected from the group consisting of N, O and S, where the $C_{1-4}$ alkyl radical can be unsubstituted or mono- or polysubstituted by identical or different substituents from the group consisting of $C_{1-6}$ alkyl, halogen or oxo (=O) and where the $C_{6-14}$ aryl or $C_{2-10}$ heteroaryl radical can be unsubstituted or mono- or polysubstituted by identical or different substituents from the group consisting of straight-chain or branched $C_{1-8}$ alkyl, $C_{3-7}$ cycloalkyl, halogen, cyano, $C_{1-6}$ alkoxycarbonylamino, $C_{1-6}$ alkoxy, carboxyl, $C_{1-8}$ alkoxycarbonyl, or straight-chain or branched $C_{1-6}$ alkyl which is substituted by one or more fluorine atoms, hydroxyl, straight-chain or branched $C_{1-8}$ alkoxy, where adjacent oxygen atoms can also be linked by $C_{1-2}$ alkylene groups, benzyloxy, nitro, amino, mono-$C_{1-4}$ alkylamino, di-$C_{1-4}$ alkylamino, or aryl, which can be unsubstituted or mono- or polysubstituted by identical or different substituents from the group consisting of straight-chain or branched $C_{1-8}$ alkyl, $C_{3-7}$ cycloalkyl, carboxyl, straight-chain or branched $C_{1-8}$ alkoxycarbonyl, trifluoromethyl, hydroxyl, straight-chain or branched $C_{1-8}$ alkoxy, benzyloxy, nitro, amino, mono-$C_{1-4}$ alkylamino, di-$C_{1-4}$ alkylamino, cyano, straight-chain or branched cyano-$C_{1-6}$ alkyl;
and their structural isomers and stereoisomers and their pharmaceutically acceptable salts;
wherein said tumor is selected from the group consisting of cervical carcinoma, lymphocyte leukemia, breast adenocarcinoma, ovarian adenocarcinoma, and pulmonary carcinoma.

14. The method of claim 13, wherein $R_4$ is a straight-chain or branched $C_{2-20}$ alkenyl or alkynyl which can be unsubstituted or can optionally be substituted at the same or different C atoms by one, two or more aryl, heteroaryl, halogen, cyano, $C_{1-6}$ alkoxycarbonylamino, $C_{1-6}$ alkoxy, amino, mono-$C_{1-4}$ alkylamino or di-$C_{1-4}$ alkylamino; a straight-chain or branched $C_{1-20}$ alkyl which can be unsubstituted or can optionally be substituted at the same or different C atoms by two or more aryl, heteroaryl, halogen, cyano, $C_{1-6}$ alkoxycarbonylamino, $C_{1-6}$ alkoxy, amino, mono-$C_{1-4}$ alkylamino or di-$C_{1-4}$ alkylamino; a straight-chain or branched $C_{1-20}$ alkyl which can be unsubstituted or can optionally be substituted at the same or different C atoms by one heteroaryl halogen, cyano, $C_{1-6}$ alkoxycarbonylamino, $C_{1-6}$ alkoxy, amino, mono-$C_{1-4}$ alkylamino or di-$C_{1-4}$ alkylamino; a $C_{6-14}$ aryl radical, or a $C_{2-10}$ heteroaryl or $C_{2-10}$ heteroaryl-$C_{1-4}$ alkyl radical which contains one or more heteroatoms selected from the group consisting of N, O and S, here the $C_{1-4}$ alkyl radical can be unsubstituted or mono- or polysubstituted by identical or different substituents from the group consisting of $C_{1-6}$ alkyl, halogen or oxo (=O) and where the $C_{6-14}$ aryl or $C_{2-10}$ heteroaryl radical can be unsubstituted or mono- or polysubstituted by identical or different substituents from the group consisting of straight-chain or branched $C_{1-8}$ alkyl, $C_{3-7}$ cycloalkyl, halogen, cyano, $C_{1-6}$ alkoxycarbonylamino, $C_{1-6}$ alkoxy, carboxyl, $C_{1-8}$ alkoxycarbonyl, or straight-chain or branched $C_{1-6}$ alkyl which is substituted by one or more fluorine atoms, hydroxyl, straight-chain or branched $C_{1-8}$ alkoxy, where adjacent oxygen atoms can also be linked by $C_{1-2}$ alkylene groups, benzyloxy, nitro, amino, mono-$C_{1-4}$ alkylamino, di-$C_{1-4}$ alkylamino, or aryl, which can be unsubstituted or mono- or polysubstituted by identical or different substituents from the group consisting of straight-chain or branched $C_{1-8}$ alkyl, $C_{3-7}$ cycloalkyl, carboxyl, straight-chain or branched $C_{1-8}$ alkoxycarbonyl, trifluoromethyl, hydroxyl, straight-chain or branched $C_{1-8}$ alkoxy, benzyloxy, nitro, amino, mono-$C_{1-4}$ alkylamino, di-$C_{1-4}$ alkylamino, cyano, straight-chain or branched cyano-$C_{1-6}$ alkyl; or $C_{6-14}$ aryl-$C_{1-4}$ alkyl radical, where the $C_{1-4}$ alkyl radical can be unsubstituted or mono- or polysubstituted by identical or different substituents from the group consisting of $C_{1-6}$ alkyl, halogen or oxo (=O) and where the $C_{6-14}$ aryl is be mono- or polysubstituted by identical or different substituents from the group consisting of straight-chain or branched $C_{1-8}$ alkyl, $C_{3-7}$ cycloalkyl, halogen, cyano, $C_{1-6}$ alkoxycarbonylamino, carboxyl, $C_{1-8}$ alkoxycarbonyl, or straight-chain or branched $C_{1-6}$ alkyl which is substituted by one or more fluorine atoms, hydroxyl, straight-chain or branched $C_{1-8}$ alkoxy, where adjacent oxygen atoms can also be linked by $C_{1-2}$ alkylene groups, benzyloxy, nitro, amino, mono-$C_{1-4}$ alkylamino, di-$C_{1-4}$ alkylamino, or aryl, which can be unsubstituted or mono- or polysubstituted by identical or different substituents from the group consisting of straight-chain or branched $C_{1-8}$ alkyl, $C_{3-7}$ cycloalkyl, carboxyl, straight-chain or branched $C_{1-8}$ alkoxycarbonyl, trifluoromethyl, hydroxyl, straight-chain or branched $C_{1-8}$ alkoxy, benzyloxy, nitro, amino, mono-$C_{1-4}$ alkylamino, di-$C_{1-4}$ alkylamino, cyano, straight-chain or branched cyano-$C_{1-6}$ alkyl.

* * * * *